(12) United States Patent
Jia et al.

(10) Patent No.: US 10,896,490 B2
(45) Date of Patent: Jan. 19, 2021

(54) SYSTEMS AND METHODS FOR REFLECTANCE-BASED PROJECTION-RESOLVED OPTICAL COHERENCE TOMOGRAPHY ANGIOGRAPHY

(71) Applicant: Oregon Health & Science University, Portland, OR (US)

(72) Inventors: Yali Jia, Portland, OR (US); Jie Wang, Portland, OR (US)

(*) Notice: Subject to any disclaimer, the term of this patent is extended or adjusted under 35 U.S.C. 154(b) by 444 days.

(21) Appl. No.: 15/852,521

(22) Filed: Dec. 22, 2017

(65) Prior Publication Data
US 2018/0182082 A1   Jun. 28, 2018

Related U.S. Application Data

(60) Provisional application No. 62/438,930, filed on Dec. 23, 2016.

(51) Int. Cl.
*G06T 5/00* (2006.01)
*A61B 5/00* (2006.01)
(Continued)

(52) U.S. Cl.
CPC .............. *G06T 5/009* (2013.01); *A61B 3/102* (2013.01); *A61B 5/0066* (2013.01);
(Continued)

(58) Field of Classification Search
CPC ......... G06T 5/00; G06T 5/009; G06T 7/0012; G06T 2207/10101; A61B 5/0066;
(Continued)

(56) References Cited

U.S. PATENT DOCUMENTS 6,463,173 B1 * 10/2002 Tretter ................... G06T 5/009
382/162
7,301,644 B2 * 11/2007 Knighton ........... G01B 9/02089
356/479

(Continued)

OTHER PUBLICATIONS

Kartakoullis ["Scatterer Size-Based Analysis of Optical Coherence Tomography Images Using Spectral Estimation Techniques" Apr. 26, 2010 / vol. 18, No. 9 / Optics Express 9181]. (Year: 2010).*

(Continued)

*Primary Examiner* — Oommen Jacob

(57) ABSTRACT

Embodiments provide systems and methods associated with a reflectance-based projection-resolved (rbPR) optical coherence tomography angiography (OCTA) algorithm which uses optical coherence tomography (OCT) reflectance to enhance the flow signal and suppress the projection artifacts in 3-dimensional OCTA. rbPR improves the vascular connectivity and improved the discrimination of the deeper plexus angiograms in healthy eyes, compared to prior PR-OCTA method. Additionally, rbPR removes flow projection artifacts more completely from the outer retinal slab in the eyes with age-related macular degeneration, and preserves vascular integrity of the intermediate and deep capillary plexuses in the eyes with diabetic retinopathy. Additionally, the rbPR method improves the resolution of the choriocapillaris and demonstrates details comparable to scanning electron microscopy.

16 Claims, 16 Drawing Sheets

(51) Int. Cl.
  *G06T 7/00* (2017.01)
  *A61B 3/10* (2006.01)
  *A61B 5/02* (2006.01)
(52) U.S. Cl.
  CPC .......... *A61B 5/7203* (2013.01); *A61B 5/7271* (2013.01); *G06T 7/0012* (2013.01); *A61B 5/02007* (2013.01); *A61B 2576/02* (2013.01); *G06T 2207/10101* (2013.01)
(58) Field of Classification Search
  CPC ..... A61B 3/102; A61B 5/7203; A61B 5/7271; A61B 5/02007; A61B 2576/02
  USPC ........................................ 600/425, 424, 407
  See application file for complete search history.

(56) References Cited

U.S. PATENT DOCUMENTS

| | | | | |
|---|---|---|---|---|
| 8,079,711 | B2* | 12/2011 | Stetson | A61B 3/102 351/205 |
| 8,090,177 | B2* | 1/2012 | Venkataraman | G06T 7/11 382/130 |
| 8,260,393 | B2* | 9/2012 | Kamath | A61B 5/14532 600/347 |
| 8,625,104 | B2* | 1/2014 | Izatt | A61B 3/102 356/497 |
| 10,022,047 | B2* | 7/2018 | Yamashita | A61B 3/102 |
| 10,231,619 | B2* | 3/2019 | Huang | G06T 5/002 |
| 10,402,965 | B1* | 9/2019 | Bagherinia | G06T 7/0012 |
| 2006/0119858 | A1* | 6/2006 | Knighton | G01B 9/02091 356/479 |
| 2006/0262966 | A1* | 11/2006 | Eck | A61B 6/12 382/128 |
| 2007/0046948 | A1* | 3/2007 | Podoleanu | A61B 3/102 356/497 |
| 2007/0103693 | A1* | 5/2007 | Everett | A61B 5/0066 356/479 |
| 2007/0115481 | A1* | 5/2007 | Toth | A61B 3/0025 356/511 |
| 2008/0013093 | A1* | 1/2008 | Izatt | A61B 5/0059 356/456 |
| 2008/0031521 | A1* | 2/2008 | Can | G06K 9/0061 382/173 |
| 2008/0037897 | A1* | 2/2008 | Chiang | G06T 5/40 382/273 |
| 2008/0100612 | A1* | 5/2008 | Dastmalchi | A61B 3/102 345/418 |
| 2008/0170204 | A1* | 7/2008 | Podoleanu | A61B 3/102 351/206 |
| 2009/0268162 | A1* | 10/2009 | Stetson | A61B 3/102 351/246 |
| 2009/0270738 | A1* | 10/2009 | Izatt | A61B 5/0059 600/476 |
| 2010/0189334 | A1* | 7/2010 | Tomidokoro | A61B 3/102 382/131 |
| 2011/0034803 | A1* | 2/2011 | Stetson | G06T 15/08 600/425 |
| 2011/0038517 | A1* | 2/2011 | Mistretta | A61B 6/12 382/128 |
| 2011/0243408 | A1* | 10/2011 | Takama | A61B 3/102 382/128 |
| 2012/0063660 | A1* | 3/2012 | Imamura | G01B 9/02091 382/131 |
| 2012/0150029 | A1* | 6/2012 | Debuc | A61B 3/102 600/425 |
| 2012/0194783 | A1* | 8/2012 | Wei | A61B 3/102 351/206 |
| 2013/0094720 | A1* | 4/2013 | Stetson | G06T 15/08 382/115 |
| 2013/0286354 | A1* | 10/2013 | Stetson | A61B 3/102 351/246 |
| 2013/0301000 | A1* | 11/2013 | Sharma | A61B 3/102 351/206 |
| 2013/0301008 | A1* | 11/2013 | Srivastava | G01B 9/02083 351/246 |
| 2014/0073917 | A1* | 3/2014 | Huang | A61B 5/7246 600/427 |
| 2014/0228681 | A1* | 8/2014 | Jia | G01B 9/02091 600/425 |
| 2016/0000368 | A1* | 1/2016 | Wang | A61B 5/418 600/425 |
| 2016/0284085 | A1* | 9/2016 | Huang | G06T 7/0016 |
| 2017/0132793 | A1* | 5/2017 | Hu | G06T 7/12 |
| 2018/0182082 | A1* | 6/2018 | Jia | G06T 5/009 |

OTHER PUBLICATIONS

Girard ["Shadow Removal and Contrast Enhancement in Optical Coherence Tomography Images of the Human Optic Nerve Head", Investigative Ophthalmology & Visual Science, Sep. 2011, vol. 52, No. 10]. (Year: 2011).*

Zhang [Projection-resolved Optical Coherence Tomographic Angiography, 2016 OSA Mar. 1, 2016 | vol. 7, No. 3 | DOI:10.1364/BOE.7.000816 | Biomedical Optics Express 816]. (Year: 2016).*

Gao ["Optical Coherence Tomography Angiography" iovs.arvojournals.org j ISSN: 1552-5783, 2016] (Year: 2016).*

Yali ["Quantitative OCT angiography of optic nerve head blood flow" Dec. 1, 2012 / vol. 3, No. 12 / Biomedical Optics Express 3127] (Year: 2012).*

Wolff ["En Face OCT Imaging for the Diagnosis of Outer Retinal Tubulations in Age-Related Macular Degeneration", Journal of Ophthalmology vol. 2012, Article ID 542417, 3 pages] (Year: 2012).*

Miwa ["Relationship between Functional and Structural Changes in Diabetic Vessels in Optical Coherence Tomography Angiography" Scientific Reports | 6:29064 | DOI: 10.1038/srep29064 Mar. 2016] (Year: 2016).*

Zhang Q [Minimizing projection artifacts for accurate presentation of choroidal neovascularization in OCT micro-angiography, Biomedical Optics Express • Oct. 2015] (Year: 2015).*

Huang [Optical Coherence Tomography, Science. Nov. 22, 1991; 254(5035): 1178-1181.] (Year: 1991).*

Huang [OCT Terminology—Demystified, Apr. 1, 2009] (Year: 2009).*

Spaide ["Image Artifacts in Optical Coherence Angiography", Retina. Nov. 2015; 35(11): 2163-2180] (Year: 2015).*

Arici ["A Histogram Modification Framework and Its Application for Image Contrast Enhancement", ], IEEE Transactions on Image Processing, vol. 18, No. 9, Sep. 2009 (Year: 2009).*

Boudra ["Automated segmentation of multiple sclerosis lesions in multispectral MR imaging using fuzzy clustering", Computers in Biology and Medicine 30 (2000) 23±40] (Year: 2000).*

Chen ["Gray-Level Grouping (GLG): An Automatic Method for Optimized Image Contrast Enhancement—Part I: The Basic Method", IEEE Transactions on Image Processing, vol. 15, No. 8, Aug. 2006] (Year: 2006).*

Chitwong ["Local Area Histogram Equalization Based Multispectral Image Enhancement From Clustering Using Competitive Hopfield Neural Network", CCECE 2003-CCGEI 2003, Montrkal, Mayimai 2003] (Year: 2003).*

Govind ["Medical Image Enhancement by Applying Averaging Method in Clusters" 2013 International Conference on Advanced Computing and Communication Systems (ICACCS-2013), Dec. 19-21, 2013] (Year: 2013).*

Jafar ["New algorithms for contrast enhancement in grayscale images based on the variational definition of histogram equalization", Integrated Computer-Aided Engineering 15 (2008) 131-147] (Year: 2008).*

Tai ["Contrast Enhancement through Clustered Histogram Equalization", Research Journal of Applied Sciences, Engineering and Technology 4(20): 3965-3968, 2012 (Year: 2012).*

* cited by examiner

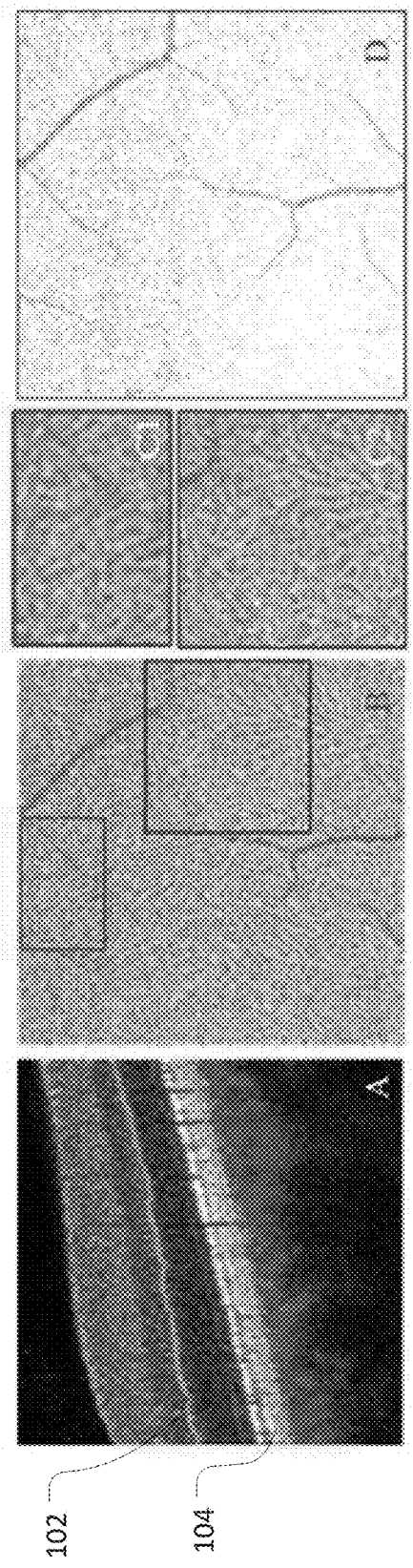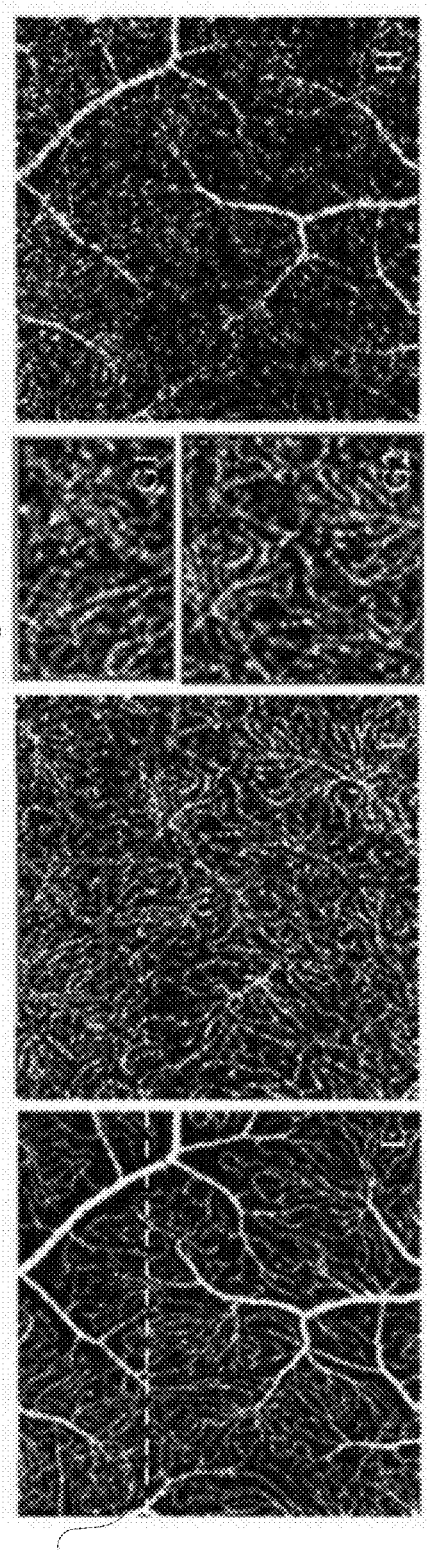

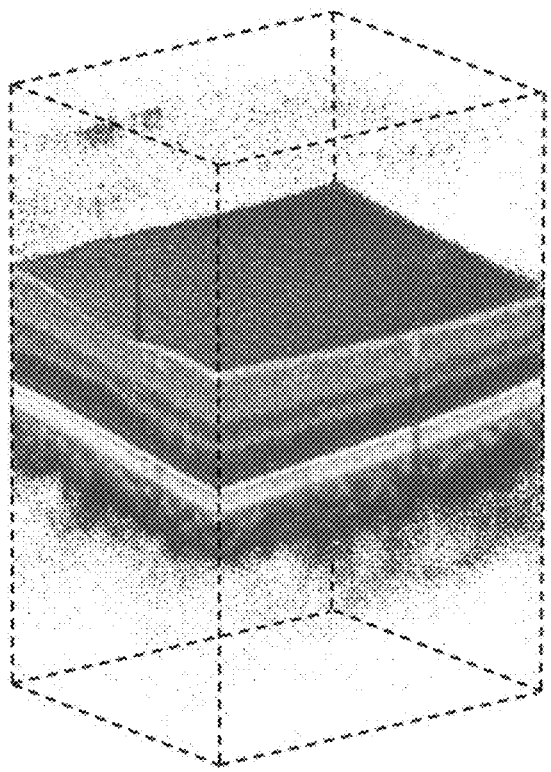
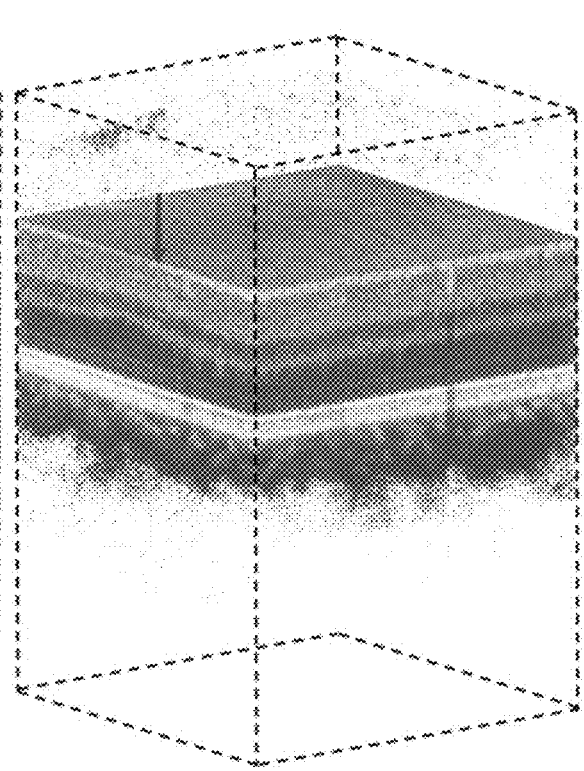
Figure 3A                     Figure 3B
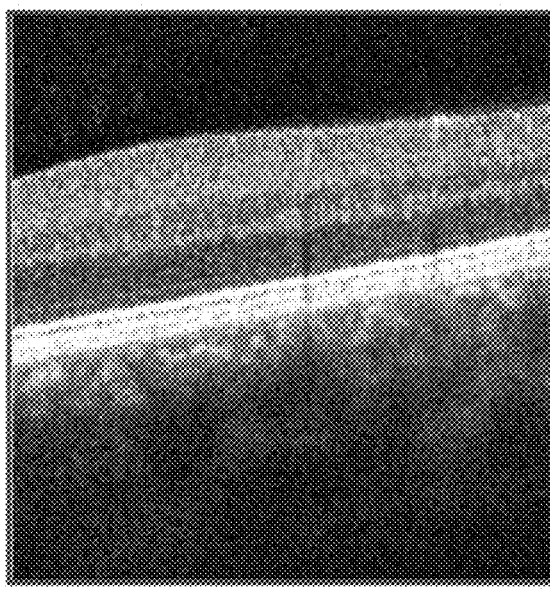
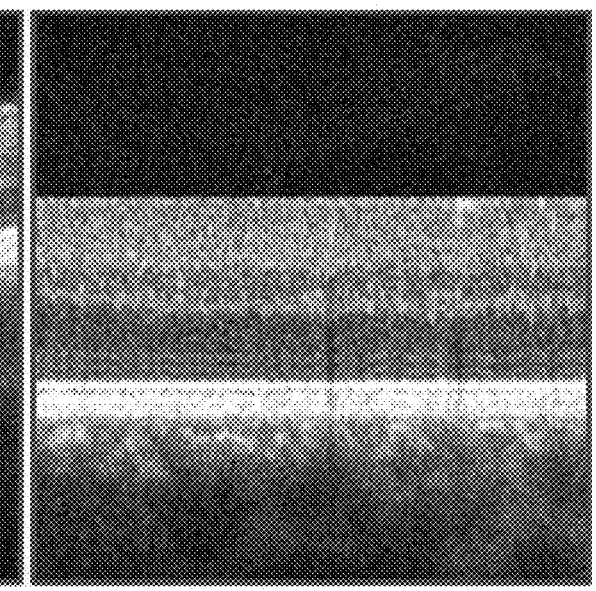
Figure 3C                     Figure 3D

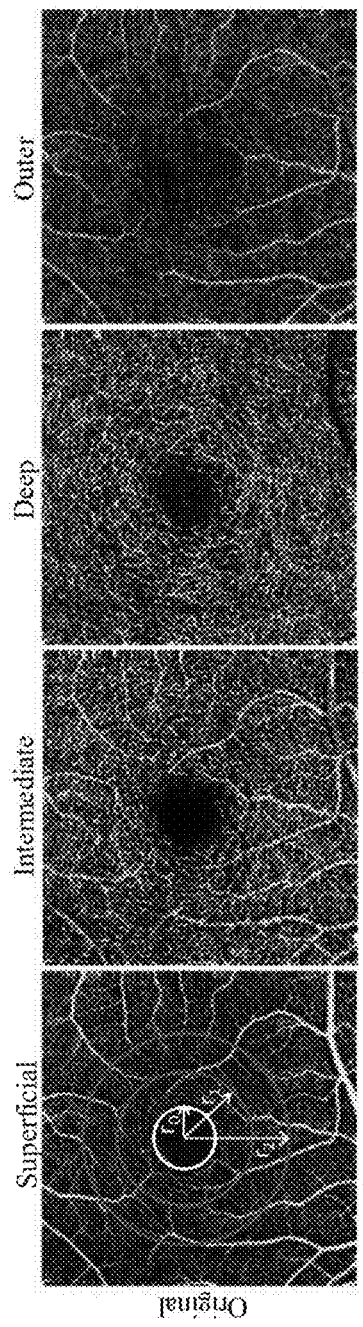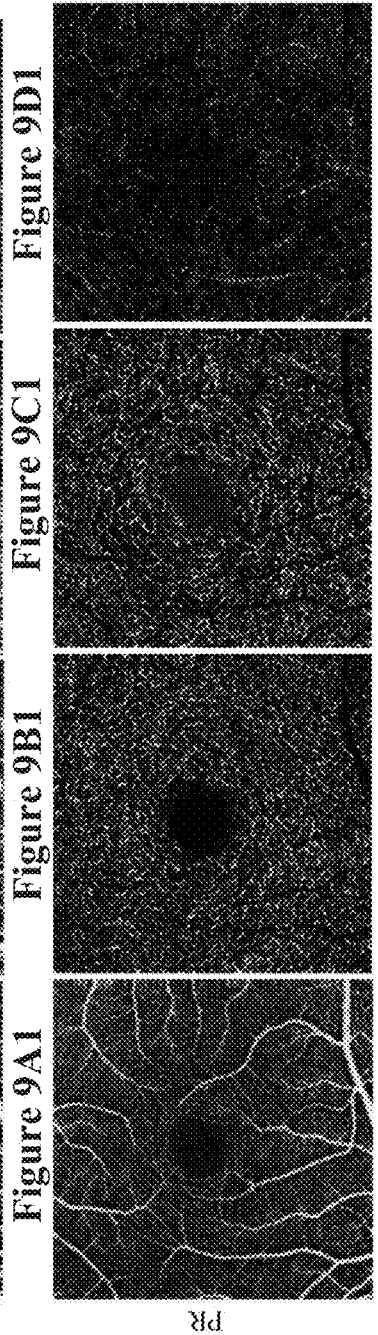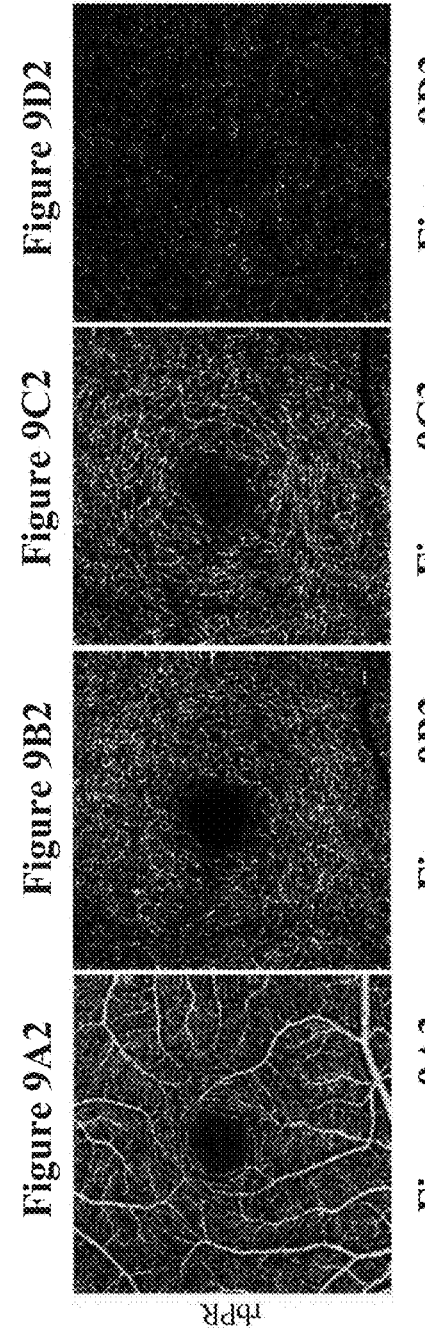

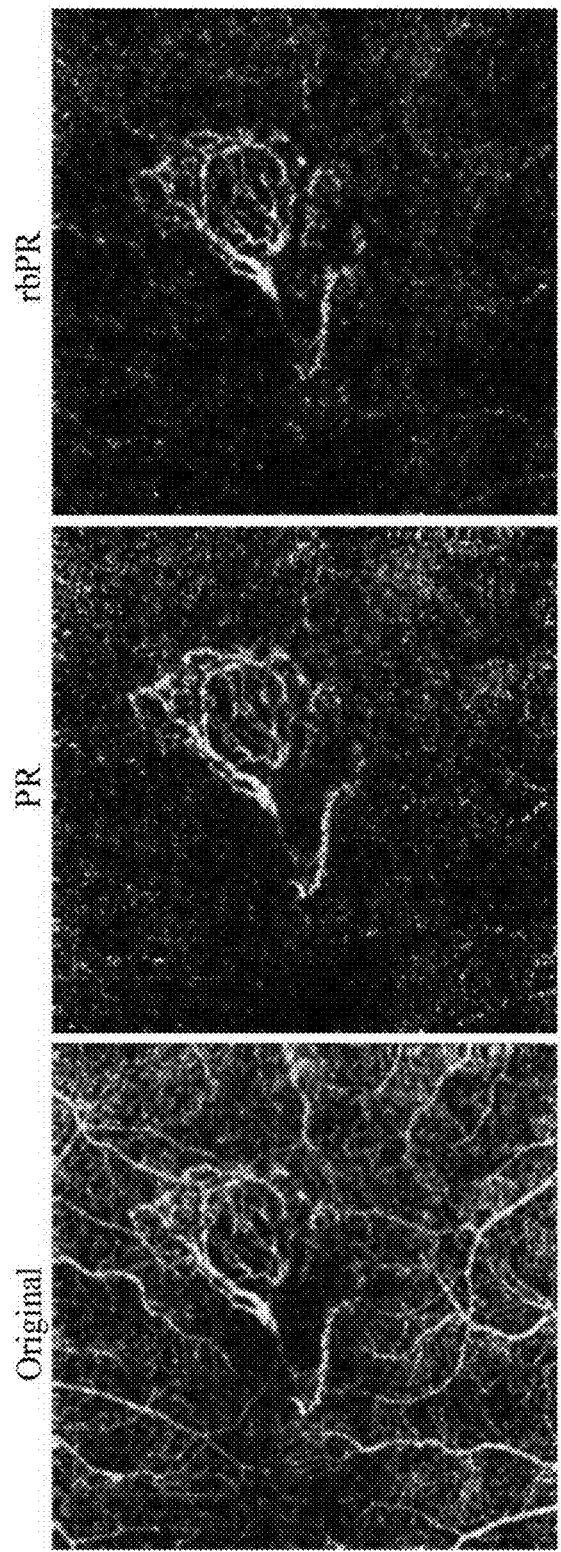
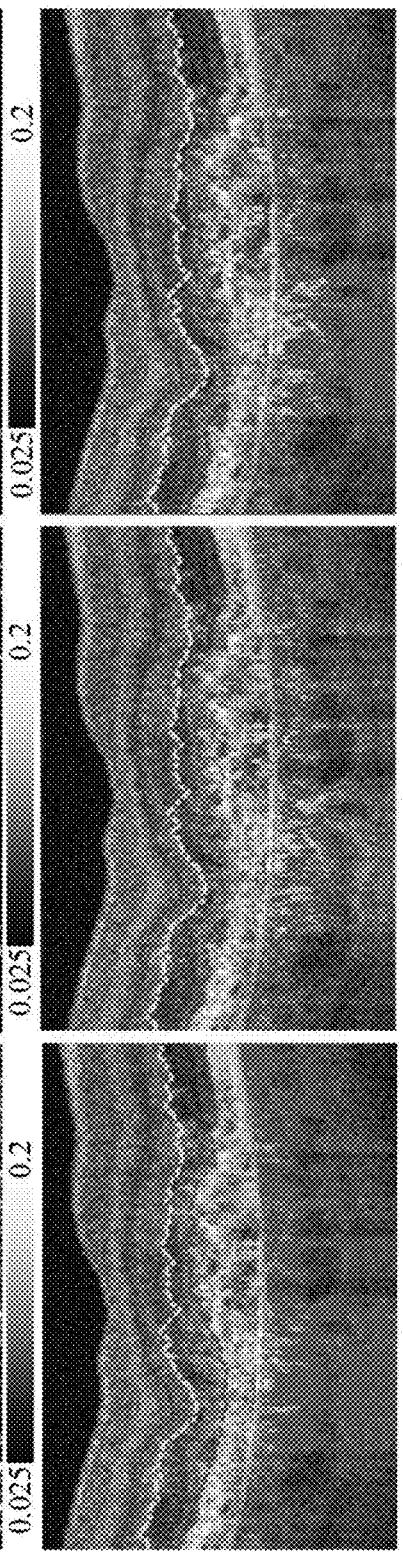

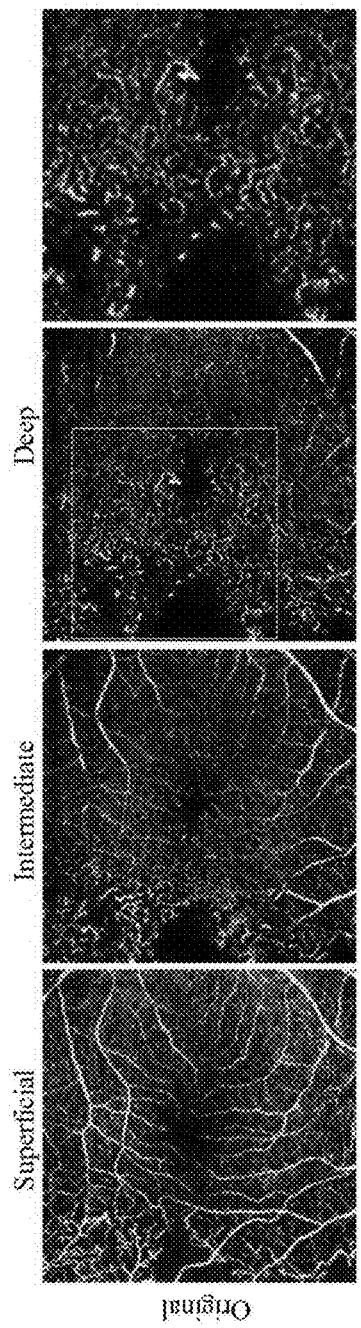

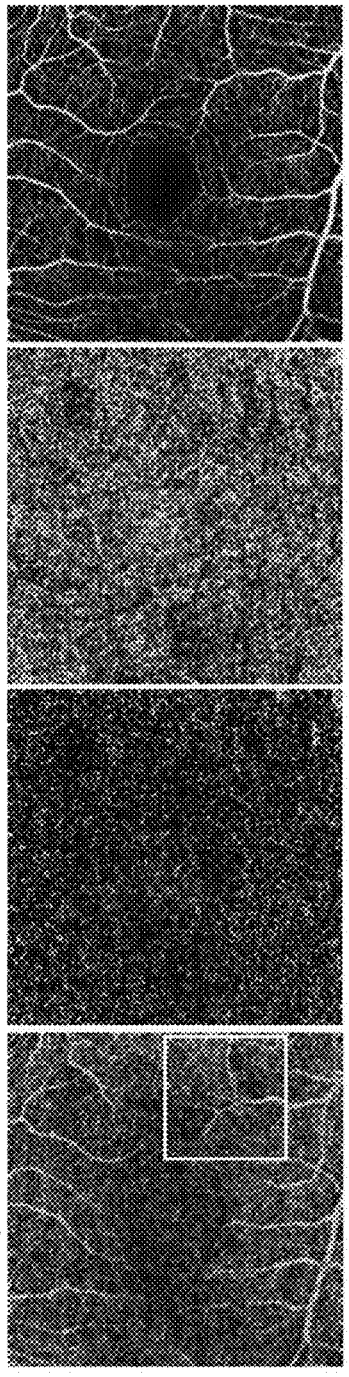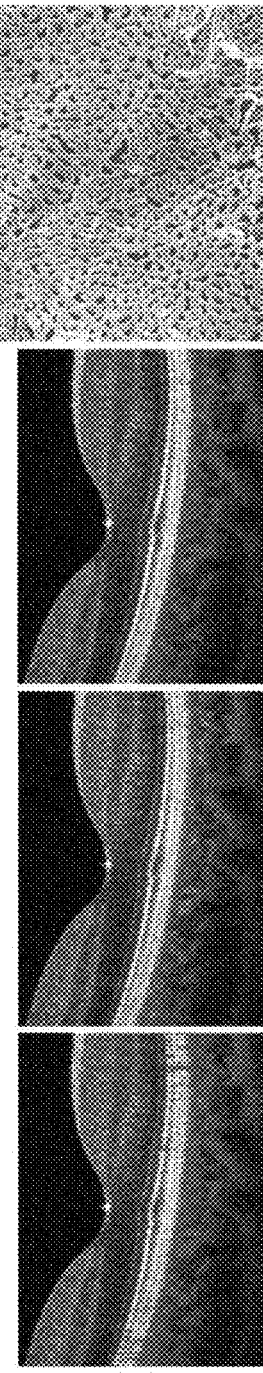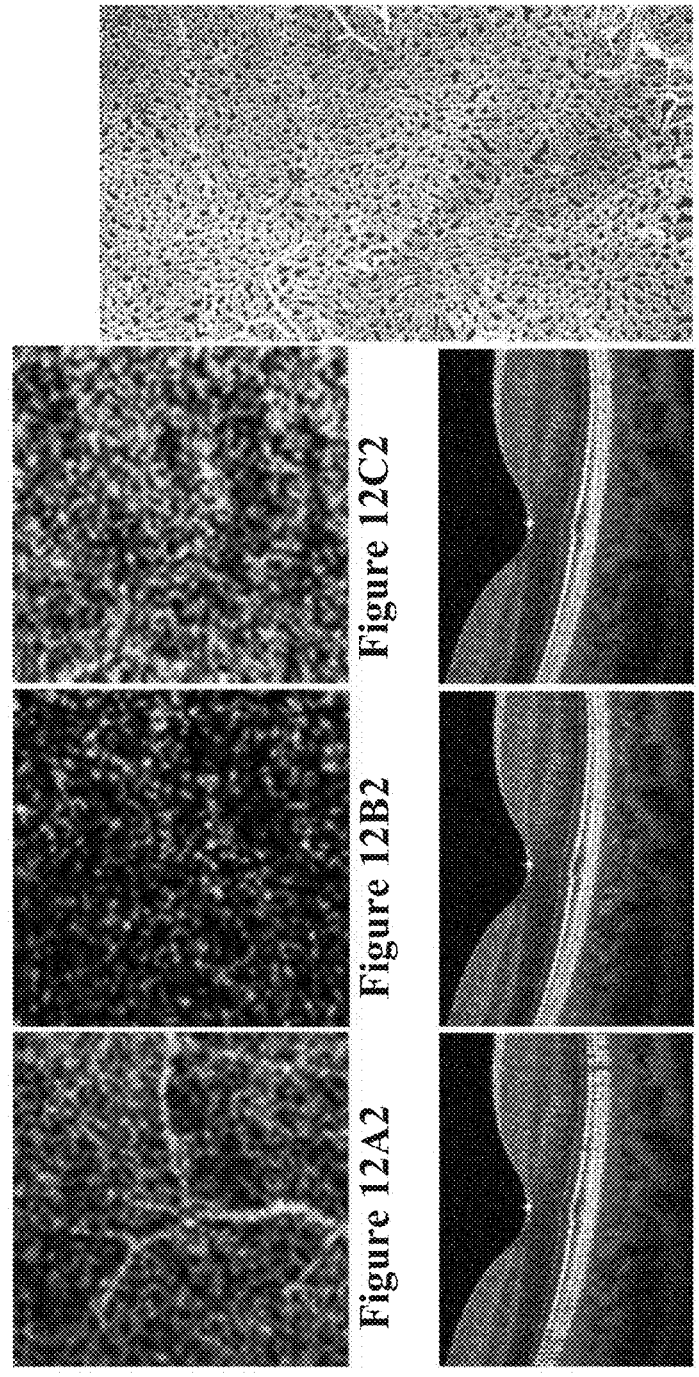
Figure 12A1, Figure 12B1, Figure 12C1, Figure 12D
Figure 12A2, Figure 12B2, Figure 12C2, Figure 12E
Figure 12A3, Figure 12B3, Figure 12C3

SYSTEMS AND METHODS FOR REFLECTANCE-BASED PROJECTION-RESOLVED OPTICAL COHERENCE TOMOGRAPHY ANGIOGRAPHY

CROSS REFERENCE TO RELATED APPLICATION

The present application claims priority to U.S. Provisional Patent Application No. 62/438,930, titled "SYSTEMS AND METHODS FOR REFLECTANCE-BASED PROJECTION-RESOLVED OPTICAL COHERENCE TOMOGRAPHY ANGIOGRAPHY," filed Dec. 23, 2016, the disclosure of which is hereby incorporated by reference in its entirety.

ACKNOWLEDGEMENT OF GOVERNMENT SUPPORT

This invention was made with government support under EY024544 and DK104397 awarded by the National Institutes of Health. The government has certain rights in the invention.

TECHNICAL FIELD

Embodiments herein relate to the field of medical imaging, and, more specifically, to optical coherence tomography (OCT) angiography.

BACKGROUND

Optical coherence tomography angiography (OCTA) is a non-invasive 3-dimensional (3D) tool for imaging retinal and choroidal microvascular networks in vivo. It detects flow by evaluating the change in reflectance from sequentially acquired structural OCT images. The 3D nature of the technique allows separate visualization of specified vascular layers. However, the depth resolution of OCTA is limited by the shadowgraphic flow projection artifact, which comes from the time-varying shadows cast by the more superficial blood vessels. On cross-sectional angiograms, this artifact appears as the flow tails below in situ blood vessels; on en face angiograms, the more superficial plexuses are projected on deeper plexuses. This inability to distinguish between projection artifact and in situ flow has confounded the 3D interpretation of OCTA.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIGS. 1A, 1B, 1C1, 1C2, 1D, 1E, 1F, 1G1, 1G2, and 1H illustrate the in situ blood flow and flow projection artifact on OCTA and their corresponding signals on structural OCT. FIG. 1A illustrates a cross-sectional structural OCT (gray) overlaid with OCTA (red). FIG. 1B illustrates a C-scan of OCT reflectance in deep plexus slab, indicated by line 102 in FIG. 1A. FIG. 1C1 and FIG. 1C2 are magnified regions of FIG. 1B to show the vessel shadow artifacts with low reflectance (outlined by green) and the capillary network with high reflectance. FIG. 1D illustrates the C-scan of OCT reflectance in outer retinal slab, indicated by line 104 in FIG. 1A. FIG. 1E illustrates the maximum projection of OCTA in superficial plexus slab, and the horizontal white dashed line 106 indicates the location of the C-scan shown in FIG. 1A. FIG. 1F illustrates the C-scan of OCTA in deep plexus slab. FIGS. 1G1 and 1G2 are magnified regions of FIG. 1F to show the real capillaries interfered by projection artifact (outlined by green). FIG. 1H shows the C-scan of OCTA in outer retinal slab.

FIG. 2 illustrates the Overview of the reflectance-based projection-resolved (rbPR) OCTA algorithm. IS/OS: junction of inner and outer photoreceptor for use to practice various embodiments.

FIGS. 3A-3D illustrate A-line resize, in accordance with various embodiments. FIG. 3A depicts the original reflectance volume; FIG. 3B depicts the volume showing resized A-scans above IS/OS; FIG. 3C depicts the B-scan of FIG. 3A indicated by the arrow in FIG. 3A; and FIG. 3D depicts the B-scan of FIG. 3B indicated by the arrow in FIG. 3B, which shows resized A-scan above the photoreceptor inner segment/outer segment (IS/OS).

FIG. 5A illustrates the C-scan of original OCT reflectance; FIG. 5B illustrates the vascular contrast enhanced C-scan; FIG. 5C illustrates the C-scan of original PR-OCTA; and FIG. 5D illustrates the C-scan processed by normalizing the C-scan of FIG. 5C with the vascular contrast enhanced C-scan of FIG. 5B. As highlighted with white outlines, the projection artifacts were removed.

FIG. 6A illustrates projection suppressed C-scan OCTA; FIG. 6B illustrates vessel probability map calculated by the reflectance; and FIG. 6C illustrates vessel enhanced vascular image by multiplying the C-scan of FIG. 6A with the vessel probability map of FIG. 6B.

FIG. 7A illustrates the original B-scan; FIG. 7B illustrates the B-scan processed by rbPR without large vessel optimization; and FIG. 7C illustrates the B-scan processed by rbPR with large vessel optimization.

FIGS. 9A1-9A3, 9B1-9B3, 9C1-9C3, and 9D1-9D3 illustrates a comparison of retinal OCTA (3×3 mm) from a normal participant processed without projection suppression (original, row 1, including FIGS. 9A1, 9B1, 9C1, and 9D1), with projection suppressed by the prior projection-resolved method (PR, row 2, including FIGS. 9A2, 9B2, 9C2, and 9D2) and the novel reflectance-based PR algorithm (rbPR, row 3, including FIGS. 9A3, 9B3, 9C3, and 9D3). Column A (including FIGS. 9A1, 9A2, and 9A3): En face OCTA of the superficial vascular plexus; Column B (including FIGS. 9B1, 9B2, and 9B3): En face OCTA of the intermediate capillary plexus; Column C (including FIGS. 9C1, 9C2, and 9C3): En face OCTA of the deep capillary plexus; and Column D (including FIGS. 9D1, 9D2, and 9D3): En face OCTA of the outer retinal slab. In FIG. 9A1, the circle with radius r0 (e.g., r0=0.3 mm) and the ring defined by radiuses r1 and r2 (e.g., r1=0.65 mm, r2=1 mm) mark the foveal avascular area and parafoveal annulus, respectively, for the measurement of flow signal to noise ratio below.

FIGS. 10A1, 10A2, 10B1, 10B2, 10C1, and 10C2 illustrate a comparison of projection-resolved (PR) algorithms in the visualization of choroidal neovascularization (CNV) on both En face (3×3 mm) and cross-sectional OCTA, in accordance with various embodiments. FIG. 10A1 is En face and FIG. 10A2 is cross-sectional OCTA of the outer retinal slab without projection suppression; FIGS. 10B1 and 10B2 correspond to the images of respective FIGS. 10A1 and 10A2 using projection suppression with the prior PR algorithm; and FIGS. 10C1 and 10C2 correspond to the images of respective FIGS. 10A1 and 10A2 using projection suppression with the reflectance-based PR (rbPR) algorithm described herein. The projection artifacts persistent on prior PR-OCTA were removed by rbPR (indicated by arrows).

FIGS. 11A1-11A3, 11B1-11B3, 11C1-11C3, and 11D1-11D3 illustrates a comparison of retinal OCTA (6×6 mm) processed without projection suppression (original, row 1, including FIGS. 11A1, 11B1, 11C1, and 11D1), with projection suppressed by the prior projection-resolved method (PR, row 2, including FIGS. 11A2, 11B2, 11C2, and 11D2) and the novel reflectance-based PR algorithm described herein (rbPR, row 3, including FIGS. 11A3, 11B3, 11C3, and 11D3). Column A (including FIGS. 11A1, 11A2, and 11A3): En face OCTA of the superficial vascular plexus; Column B (including FIGS. 11B1, 11B2, 11B3): En face OCTA of the intermediate capillary plexus; Column C (including FIGS. 11C1, 11C2, 11C3): En face OCTA of the deep capillary plexus; and Column D (including FIGS. 11D1, 11D2, and 11D3): The magnified images in the positions indicated by a white box in FIG. 11C1.

FIGS. 12A1-12A3, 12B1-12B3, 12C1-12C3, 12D, and 12E illustrate a comparison of submacular choriocapillaries OCTA processed without projection suppression (column A, including FIGS. 12A1, 12A2, and 12A3), with projection suppressed by the prior projection-resolved method (PR, column B, including FIGS. 12B1, 12B2, and 12B3), and the novel reflectance-based PR algorithm described herein (rbPR, column C, including FIGS. 12C1, 12C2, and 12C3). (FIGS. 12A1, 12B1, and 12C1): En face OCTA of the choriocapillaries plexus. (FIGS. 12A2, 12B2, and 12C2): The magnified images in the positions indicated by a white box in FIG. 12A1. (FIGS. 12A3, 12B3, and 12C3): B-scan reflectance image overlaid with flow signals. FIG. 12D illustrates an inner retinal angiogram. FIG. 12E illustrates a chriocapillaris shown by scanning electron microscopy, reproduced from Oliver et al. with permission. The scale bar is 250 μm.

DETAILED DESCRIPTION OF DISCLOSED EMBODIMENTS

Figure 2:
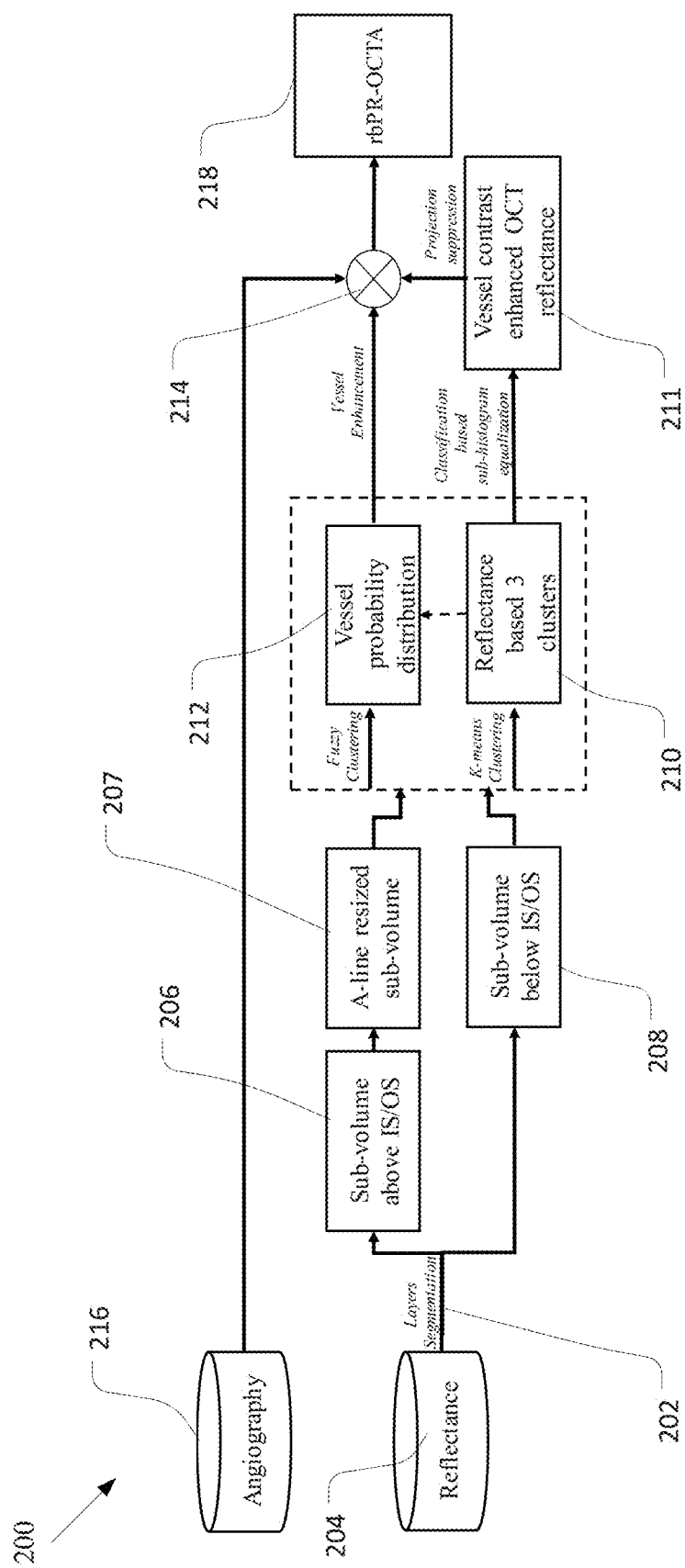

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

Embodiments herein provide systems and methods associated with a reflectance-based projection-resolved (rbPR) OCTA algorithm. A novel PR algorithm—rbPR—is presented herein, which removes flow projection artifacts and preserves in situ blood flow in OCTA better than prior methods. Several novel techniques are applied in the rbPR technique. For example, the rbPR technique takes into account OCT reflectance information in distinguishing the real vessels and flow projection on OCTA. This improves the reliability of projection resolution, compared to the methods that solely depend on OCTA. Additionally, or alternatively, a non-linear model is applied for generating the vascular contrast enhanced map and vascular probability distribution map based on OCT reflectance. This improves the vascular continuity, compared to the linear fashion method used before. Additionally, or alternatively, instead of processing the data based on a single A-line, the rbPR technique may analyze 2D images in the transverse direction slice by slice to separate in situ flow and projection artifacts. This helps to preserve the continuity of vascular networks. Furthermore, the projection resolution under larger vessels may be processed separately to minimize the negative artifact and shadowing problem.

Compared to the prior PR method, rbPR algorithm may suppress more flow projection artifacts, especially in the outer retinal slab, while preserving more blood vasculature and remaining more continuous vascular network in deeper plexuses. This is critical for the development of automatic quantification software, such as CNV detection and nonperfusion area detection on three plexuses. Similar to the prior PR method, the new rbPR method also resolves the projection artifacts on a voxel-by-voxel basis. Unlike slab-subtraction algorithm that is only applicable to en face view, rbPR allows interpretation of blood flow with respect to retinal plexuses on cross-sectional images. For example, using PR methods, the interconnecting vessels between the vascular plexuses may be distinguished.

In various embodiments, structure and/or flow information of a sample may be obtained using optical coherence tomography (OCT) (structure) and OCT angiography (flow) imaging based on the detection of spectral interference. Such imaging may be two-dimensional (2-D) or three-dimensional (3-D), depending on the application. Structural imaging may be of an extended depth range relative to prior art methods, and flow imaging may be performed in real time. One or both of structural imaging and flow imaging as disclosed herein may be enlisted for producing 2-D or 3-D images.

In order to facilitate review of the various embodiments of the disclosure, the following explanation of specific terms is provided:

A-scan: A reflectivity profile that contains information about spatial dimensions and location of structures within an item of interest. An A-scan is directed along the optical axis of the OCT device and penetrates the sample being imaged. The A-scan encodes reflectivity information (for example, signal intensity) as a function of depth.

B-scan: A cross-sectional tomograph that may be achieved by laterally combining a series of axial depth scans (i.e., A-scans). A B-scan encodes planar cross-sectional information from the sample and is typically presented as an image.

C-scan: A cross-sectional tomograph that may be achieved by laterally combining a series of axial A-scans in the transverse direction, orthogonal to the axis of the B-scan. The B-scan may be referred to as the fast scan direction, and the C-scan may be referred to as the slow scan direction.

Dataset: As used herein, a dataset is an ordered-array representation of stored data values that encodes relative spatial location in row-column-depth (x-y-z) format. In the context of OCT, as used herein, a dataset may be conceptualized as a three dimensional array of voxels, each voxel having an associated value (for example, an intensity value or a decorrelation value). An A-scan corresponds to a set of collinear voxels in the depth (axial) direction of the dataset; a B-scan is made up of set of adjacent A-scans combined in the lateral (row) direction. Such a B-scan may also be referred to as an image, and its constituent voxels referred to as pixels. A collection of adjacent B-scans can be combined in the vertical (column) direction to form a 3D volumetric set of voxel data (or 3D image). The most basic form of a dataset as used herein is a single A-scan. More typically, however, a dataset is comprised of multiple A-scans organized into one or more B-scans. Additionally, a C-scan may be a set of adjacent A-scans in the transverse (column) direction. In embodiments, the rbPR method described herein may be performed on individual C-scans.

In the systems and methods described herein, the dataset obtained by an OCT scanning device is termed a "structural OCT dataset" whose values may, for example, be complex numbers carrying intensity and phase information. This structural OCT dataset can be used to calculate a corresponding dataset termed an "OCT angiography dataset" of decorrelation values reflecting flow within the imaged sample. There is a one-to-one correspondence between the voxels of the structural OCT dataset and the OCT angiography dataset. Thus, values from the datasets may be "overlaid" to present composite images of structure and flow (e.g., tissue microstructure and blood flow).

Optical coherence tomography (OCT) is an optical signal acquisition and processing method that is capable of capturing micrometer-resolution, two- and three-dimensional images from within optical scattering media, e.g., biological tissue. Optical coherence tomography is based on interferometric techniques and typically employs near-infrared light. The use of relatively long wavelength light allows it to penetrate into the scattering medium. As remarked above, among its many applications, OCT-based ocular imaging has found widespread clinical use and can be performed quickly and easily with minimal expertise. OCT is a non-invasive imaging modality which provides accurate and precise anatomical reproduction of the retinal layers thus is well suited for use in detecting and diagnosing diseases of the retina.

In recent years, OCT techniques have been extended to allow the detection of flow within scattering media, typically using speckle variance, decorrelation, phase-difference, or other approaches. Collectively these techniques are termed "OCT angiography" when applied to the detection of microcirculation within biological tissues. OCT angiography provides the ability to noninvasively map vasculature and microvascular beds within tissues. Applied to the retina, OCT angiography is well suited for visualizing and quantifying the integrity of retinal circulation pathways and for detecting abnormalities in ocular hemodynamics and vascular structure.

OCT angiography algorithms detect decorrelation (speckle variance) in OCT intensity or phase over time within an imaged sample to separate blood flow from static tissue. This speckle variance may be produced directly by the flow of RBCs within vascular structures, or may arise indirectly by flickering shadows cast by the flow in the path of the beam. Thus, during OCT image acquisition blood vessels in the superficial layers of the retina cast shadowgraphic flow projection artifacts onto the deeper layers. These flow projection artifacts cause difficulties with the separation of different capillary plexi located at different depths in the retina, hindering detection of vascular abnormalities that might occur in deeper layers. For instance, pathological choroidal neovascularization in the outer retina may be difficult to discern due to the masking effect of overlying shadowgraphic flow projection artifacts from the vasculature of the more superficial inner retina.

Initial efforts to suppress projection artifacts from OCTA have relied on the subtraction of superficial signal from deeper slabs. Some have enhanced this technique by factoring in the structural OCT information. These slab subtraction (SS) algorithms require correct segmentation of the vascular layers, which can be problematic in diseased eyes with distorted anatomy. SS also frequently replaces projection artifact with artificial shadows, interrupting the vascular integrity of the deeper layers. Additionally, SS algorithms remove the artifacts only in en face angiograms, making cross-sectional angiograms difficult to interpret due to projection artifacts.

Recently, the present inventors proposed a projection-resolved (PR) OCTA algorithm that resolves the ambiguity between in situ flow and projection artifact at the level of single voxels, rather than conventional projection removal by SS. This method is based on the observation that normalized projection artifact signal is less than the value of the original signal. Hence, at each A-scan, signal peaks are successively analyzed, selectively removing those with lesser values than more superficial peaks. The resulting 3D macular angiogram demonstrates 3 distinct retinal vascular plexuses in their true anatomic location, consistent with known histopathology. Even with this method, the continuity of the deeper vasculature is not fully preserved. This is due to an algorithm that relies on A-scans only and assigns decorrelation values of the successive peak positions in a binary fashion.

The rbPR OCTA algorithm described herein improves projection resolution outcomes by using the structural OCT reflectance signal, as further described herein. The rbPR OCTA algorithm may be applied to a reflectance signal in a structural OCT volume. In some embodiments, the structural OCT volume may correspond to the region of ILM-0.16 mm to BM+0.25 mm. In various embodiments, the reflectance signal may be divided into multiple regions according to the reflectance values. For example, the reflectance signal may be divided into 3 regions/clusters, separated by boundary points $B_1$ and $B_2$, that correspond to structures of low, medium, and high reflectance, respectively. The boundary points $B_1$ and $B_2$, may be defined by k-means clustering or another comparable method, such as K-medoids, Gaussian Mixture Model (GMM), another Fuzzy C-Means (FCM)-based method, such as conditional FCM, possibilistic c-Means (PCM), or weighted PCM (WPCM). A value $C_H$ is defined as the center value (e.g., mean value) of the high reflectance cluster.

On a structural OCT C-scan, the boundary points $B_1$ and $B_2$ and Equation 3 (defined below) may be used to generate a contrast enhanced image $I_e$. The contrast enhanced image $I_e$ may better highlight capillaries and darken projection artifacts. After this is done for every C-scan in the structural OCT volume, $V_e$ is then normalized and used to scale the OCTA volume to create a new volume $A_1$.

The values between $B_1$ and $C_H$ are further classified into 2 clusters using fuzzy C-means or another comparable method. The rbPR method may define the probability, P, of a pixel/voxel as belonging to the cluster with higher reflectance. The rbPR may further set pixels/voxels with reflectance outside of the range $[B_1\ C_H]$ to have a probability of 0. P is then used to scale the normalized $A_1$ to create a new volume $A_r$.

In various embodiments, large vessels on the en face inner retinal OCTA may be identified by thresholding. For example, a voxel that has a flow signal value higher than a threshold may be considered to be associated with a large vessel. The voxels identified as large vessels may be analyzed separately by the rbPR method. For example, the reflectance signal in structural OCT A-scans with large vessels identified may be classified into 2 clusters (low reflectance and high reflectance) separated by a boundary B' (e.g., using fuzzy C-means or a comparable method). A probability, P' of a pixel/voxel as belonging to the cluster with higher reflectance is defined. The pixels/voxels with reflectance greater than $C'_H$, the mean value of the cluster with higher reflectance, are set to have a probability of 0. P' is then used to scale the corresponding A-scans with large vessels in the OCTA volume.

In accordance with one example implementation of embodiments described herein, OCTA data was acquired using 70 kHz spectral domain OCT system (RTVue-XR Avanti; Optovue, Inc., Fremont, Calif.) with a center wavelength of 840 nm. Two repeated B-scans, each consisting of 304 A-scans, were captured at each of 304 locations in 2.9 seconds. The 2×2, 3×3, or 6×6 mm scanning region was centered at the fovea. A commercial version of the split-spectrum amplitude-decorrelation angiography (SSADA) algorithm detected blood flow. One x-fast and one y-fast scans were acquired, registered, and merged, minimizing motion artifacts. The resulting images are shown in FIG. 1.

FIG. 1 illustrates the in situ blood flow and flow projection artifact on OCTA and their corresponding signals on structural OCT. FIG. 1A illustrates a cross-sectional structural OCT overlaid with OCTA. FIG. 1B illustrates a C-scan of OCT reflectance in deep plexus slab, indicated by dotted line 102 in FIG. 1A. FIG. 1C1 and FIG. 1C2 are magnified regions of FIG. 1B to show the vessel shadow artifacts with low reflectance (outlined by dashed boxes) and the capillary network with high reflectance. FIG. 1D illustrates the C-scan of OCT reflectance in outer retinal slab, indicated by dotted line 104 in FIG. 1A. FIG. 1E illustrates the maximum projection of OCTA in superficial plexus slab, and the horizontal white dashed line 106 indicates the location of the C-scan shown in FIG. 1A. FIG. 1F illustrates the C-scan of OCTA in deep plexus slab. FIGS. 1G1 and 1G2 are magnified regions of FIG. 1F to show the real capillaries interfered by projection artifact (outlined by dashed boxes). FIG. 1H shows the C-scan of OCTA in outer retinal slab.

A comparison of the C-scan (single voxel thick) of structural OCT (FIG. 1B) and OCTA (FIG. 1F) at the level of the deep plexus demonstrates that a relationship exists between the vessels, the shadow artifacts, and the projection artifacts. Due to the light attenuation, the superficial blood vessels (FIG. 1E) cast shadows in the structural OCT, creating regions with lower reflectance (shadow cast) compared to the surrounding tissue (FIGS. 1C1 and 1C2). These areas, however, look brighter in OCTA (FIGS. 1G1 and 1G2) due to projection artifacts. This relationship is more obvious in the avascular outer retinal slab (FIGS. 1D and 1H). Furthermore, the capillary patterns on OCTA (FIG. 1G2) correspond to the brighter reflectance signals on structural OCT (FIG. 1C2). In other words, real vessels correspond to high reflectance while projection artifacts have low reflectance in structural OCT. Therefore, in accordance with various embodiments described herein, OCT reflectance information obtained from the same C-scan is utilized to enhance the contrast of real blood vessels and minimize the projection artifacts. The C-scan may be a single voxel thick.

FIG. 2 is a flow chart of a process 200 that summarizes the image processing steps to realize this aim in clinical cases with varied anatomy. At 202, a structural OCT 204 is divided into multiple (e.g., two) sub-volumes (e.g., along photoreceptor inner/outer segment (IS/OS)). For example, the structural OCT 204 may be divided into a sub-volume 206 above IS/OS and a sub-volume 208 below IS/OS. The sub-volumes 206 and 208 may be processed separately by the process 200.

At 210, vessel contrast enhanced OCT reflectance 211 at each C-scan is obtained (e.g., using the K-means clustering method) for both sub-volumes 206 and 208. Additionally, at 212, a vessel probability distribution map at each C-scan may be obtained (e.g., using a fuzzy C-means method). Then, at 214, each angiographic C-scan from angiography dataset 216 is scaled by (1) normalized reflectance-based vessel contrast map (e.g., vessel contrast enhanced OCT reflectance 211) to suppress projection artifacts, and (2) vessel probability distribution map to enhance the vasculature. The result is a rbPR-OCTA dataset 218. This algorithm was implemented with custom software written in Matlab 2011a (Mathworks, Natick, Mass.) installed in a computer with Intel® Core™ CPU i7-6800K @3.4 GHZ and DDR4 32 GB RAM.

As shown at 202, the scan volume 204 is divided into two sub-volumes: above and below IS/OS volumes, and they are processed separately. The division of the sub-volumes takes advantage of the reflectance distribution of blood vessels and enables the process to better identify them from surrounding tissues. To obtain a homogeneous reflectance C-scan, all A-scans of upper sub-volume 206 (Ra) are resized to a same length Dmax (e.g., at 207, which is the maximum distance between ILM and IS/OS layers (see FIG. 3B)). The lower sub-volume 208 (Rb) has a naturally even depth and does not require an adjustment.

Figure 4A:
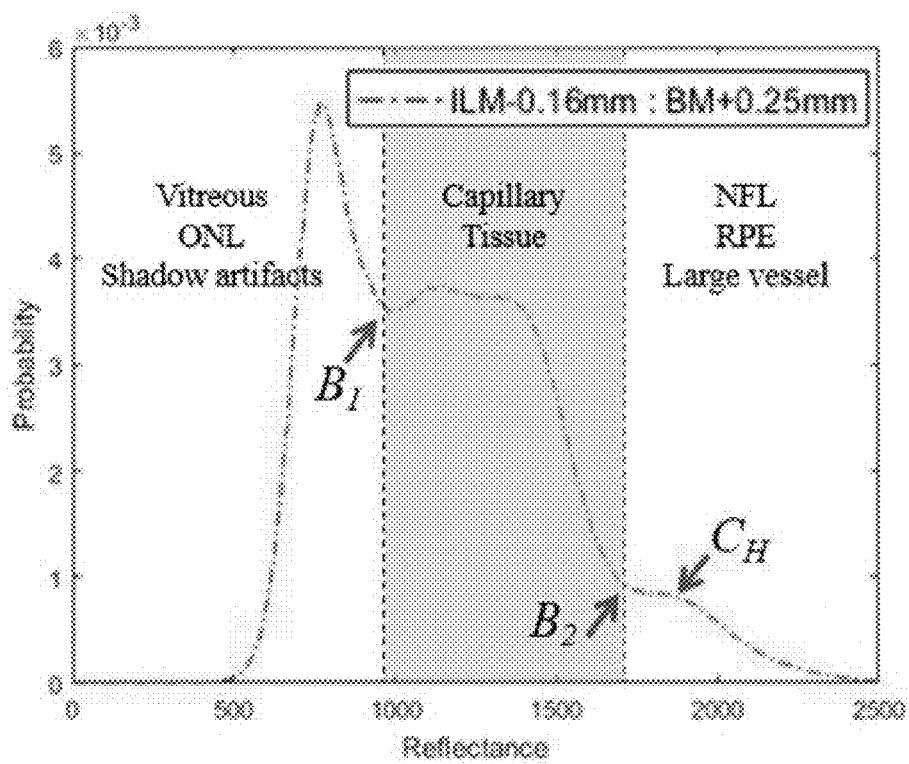
FIG. 4A illustrates reflectance distribution in whole scan volume (A)
Figure 4B:
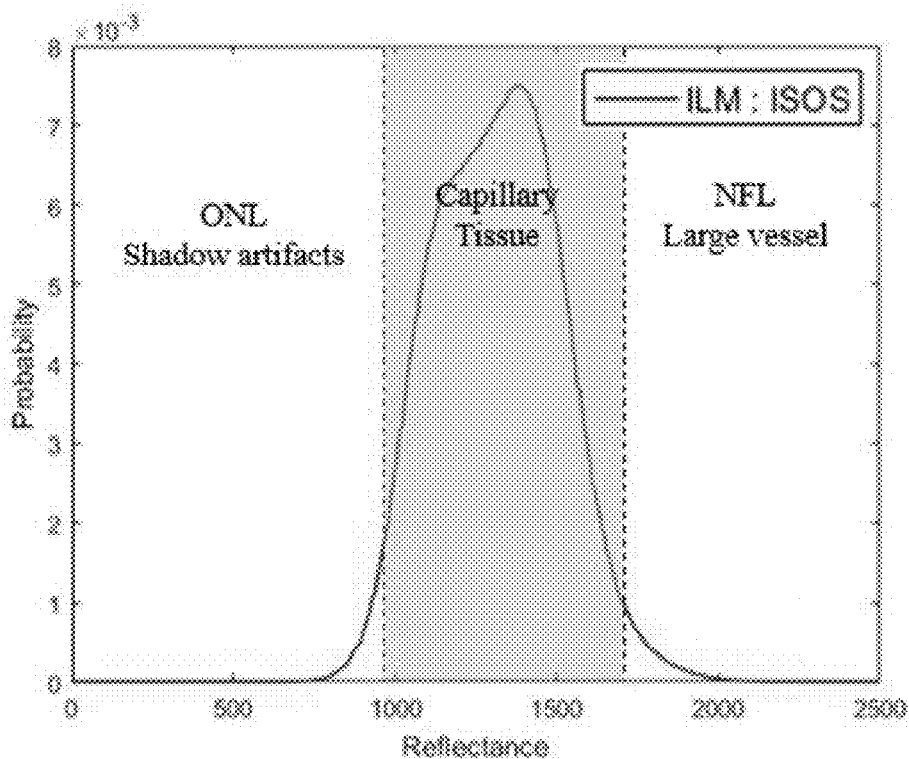
FIG. 4B illustrates reflectance distribution in volume above photoreceptor inner/outer segment (IS/OS)
Figure 4C:
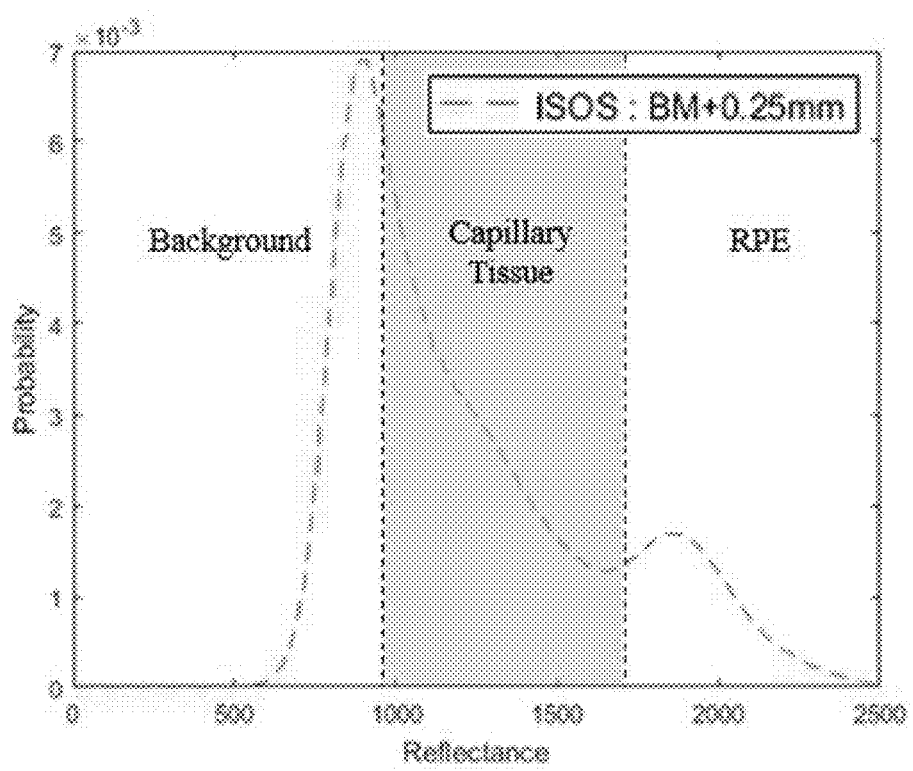
FIG. 4C illustrates reflectance distribution in volume below IS/OS, in accordance with various embodiments.

In various embodiments, the OCTA projection may be removed using vessel contrast enhanced OCT reflectance. FIG. 4 shows the reflectance histograms of the volume with 2×2 mm² scanning pattern to illustrate the reflectance distribution. For the whole retinal volume spanning 0.16 mm internal to the ILM and 0.25 mm external to BM (FIG. 4A), two inflection points ($B_1$ and $B_2$) divided the histogram into three parts: high, medium and low reflectance. The voxels of the vitreous, outer nuclear layer (ONL) and shadow artifacts have low reflectance. The reflectance of capillaries and neurosensory retina is between that of the vitreous and the retinal pigment epithelium (RPE), the nerve fiber layer (NFL) and the large vessels. The histogram of two sub-volumes divided along the IS/OS band (FIGS. 4B and 4C) confirm that capillaries have medium reflectance. Based on this insight, all voxels of each sub-volume are classified into 3 clusters by reflectance (e.g., block 210 of process 200) and the vascular component can be enhanced in the later operations.

In this section, K-means classification may be applied on each sub-volume, and the classification results may be used to divide the histogram into sub-histograms in each C-scan. Then the exposure based sub histogram equalization (ESIHE) algorithm (e.g., as described in K. Singh, and R. Kapoor, "Image enhancement using exposure based sub image histogram equalization," Pattern Recognition Letters 36, 10-14 (2014), hereby incorporated by reference herein) may be adapted to enhance the blood vessels in each C-scan.

The K-means classification method may be used to classify the volume into three clusters by minimizing the cost function:

$$LSE_1 = \sum_{k=1}^{K} \sum_{L(i)=k} \|I(i) - C_k\|^2 \qquad (1)$$

where, I(i) is the reflectance value of the i-th pixel, k is the cluster index, Ck is the mean reflectance value of the k-th cluster and label L(i) indicates which cluster the i-th voxel belongs to. K is the number of clusters, which may be 3 in this application.

The classification result may be optimized during the iteration of $$\begin{cases} L(i) = k, \operatorname*{argmin}_{k} \|I(i) - C(k)\|^2 \\ C(k) = \dfrac{\sum_{L(i)=k} I(i)}{\sum_{L(i)=k} 1} \end{cases} \qquad (2)$$

The histogram of C-scan was divided into three parts based on the boundaries of the clusters. The divided sub-histograms were equalized to enhance the contrast:

$$I_e(i) = \begin{cases} B_1 \times \sum_{n=0}^{I(i)} \dfrac{H_c(n)}{N_L}, & 0 \le I(i) \le B_1 \\ (B_1+1) + (B_2 - B_1 + 1) \sum_{n=B_1+1}^{I(i)} \dfrac{H_c(n)}{N_M}, & B_1+1 \le I(i) \le B_2 \\ (B_2+1) + (L-B_2+1) \sum_{n=B_2+1}^{I(i)} \dfrac{H_c(n)}{N_H}, & B_2+1 \le I(i) \end{cases} \qquad (3)$$

Figures 5A, 5B, 5C, 5D:
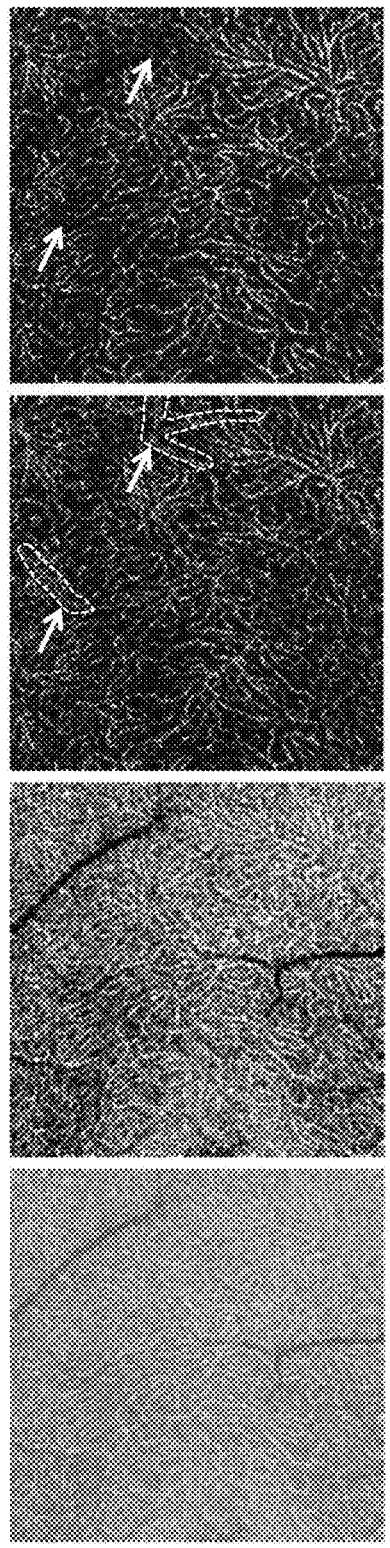
FIGS. 5A-5D illustrate OCTA normalization using vessel contrast enhanced OCT reflectance at deep capillary plexus, in accordance with various embodiments.

B1 and B2 are the reflectance of boundary points among clusters of low, medium and high reflectance. $H_c(n)$ is the original histogram, $N_L$, $N_M$ and $N_H$ are the numbers of pixels belonging to cluster of low, medium and high. n is the gray value of the reflectance, L is the gray level. Ie is the contrast enhanced image. The resulting enhanced C-scan (FIG. 5B) shows the capillaries as brighter and projection artifacts as darker compared to the original C-scan.

Repeating this process on all C-scans of the original reflectance volume ($V_o$), the vessel contrast enhanced reflectance volume ($V_e$) may be obtained. Then $V_e$ is used to suppress the projection artifacts (highlighted by arrows in FIGS. 5C and 5D) from superficial vessels (FIG. 1E) and to enhance the capillaries in the OCTA C-scans:

$$A_1 = A_o \times \text{normalized}(V_e) \qquad (4)$$

where $A_1$ is the enhanced OCTA volume, $A_0$ represent the original OCTA volume.

Figure 6C:
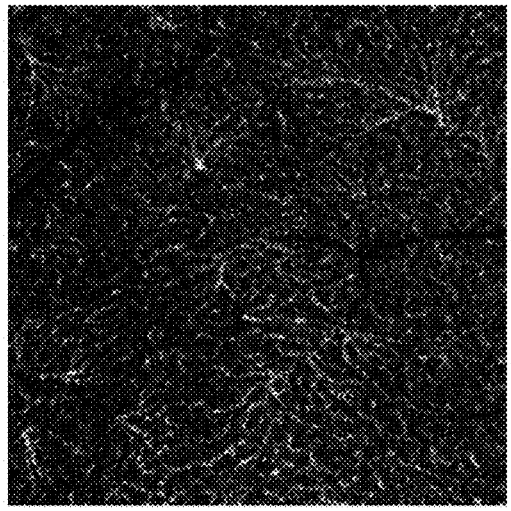
FIGS. 6A-6C illustrate vessel probability based vessel enhancement, in accordance with various embodiments.
Figure 6B:
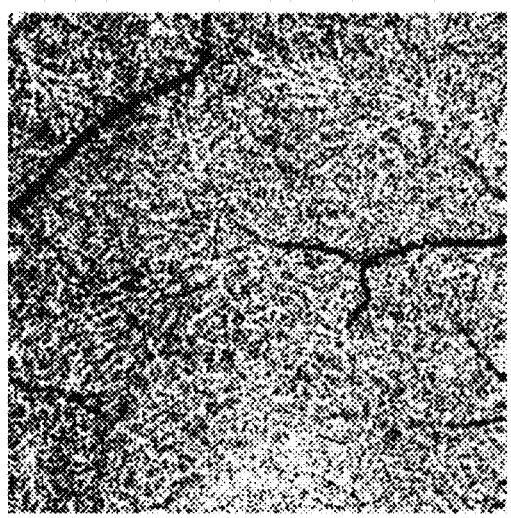

Vessel probability maps generated from each reflectance sub-volume individually can be utilized to further improve the normalized OCTA (e.g., to enhance the capillaries). Specifically, each pixel with a reflectance value between B1 (boundary value, left red arrow in FIG. 4) and CH (center value of high reflectance, right red arrow in FIG. 4) is classified into two clusters with a probability using fuzzy C-means method, yielding a probability map P, where P is the probability of pixels belonging to the cluster with higher reflectance. The pixels with a reflectance value out of the range [B1, CH] may be assigned a probability of 0. In the vessel probability map (FIG. 6B), the pixels with higher probability correspond to capillaries. Then this map can be used to further enhance the contrast of the angiogram (FIG. 6C):

$$A_r = P \times \text{Normalized}(A_1) \qquad (5)$$

Figure 6A:
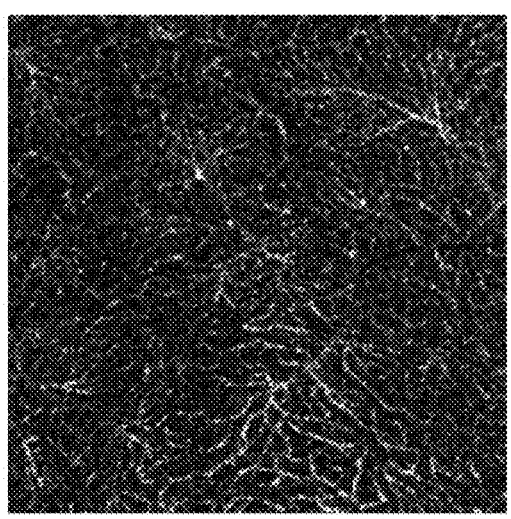

The background is darker on the representative C-scan (FIG. 6C) and the contrast between vessels and background is improved compared to the unenhanced angiogram (FIG. 6A).

Figures 7A, 7B, 7C:
FIGS. 7A-7C illustrate a B-scan reflectance image overlaid with flow signals showing large vessel optimization in rbPR algorithm, in accordance with various embodiments.

The resulting angiogram from the image processing described thus far shows a negative artifact at the larger vessels (FIG. 7B), because the reflectance of large vessel is larger than CH, and the reflectance of the region with several voxels thick just below the large vessels is between B1 and CH. Therefore, A-scans of the sub-volume containing large vessels may be processed separately to remove the negative artifacts at these vessels.

In various embodiments, large vessels may be identified on en face inner retinal OCTA by thresholding the flow signal. Then, the reflectance of A-scans in the voxels with large vessels may be classified into two clusters (low reflectance and high reflectance) at boundary B' using fuzzy C-means method with a probability. The vessel probability may be assigned to 0 if the reflectance is lower than C'h, the mean value of the cluster with high reflectance. The flow signal of the A-scans with large vessels multiplied by the vessel probability produces an angiogram with the large vessels at the correct anatomic location without the negative artifact (see FIG. 7C).

Figures 8A, 8B, 8C:
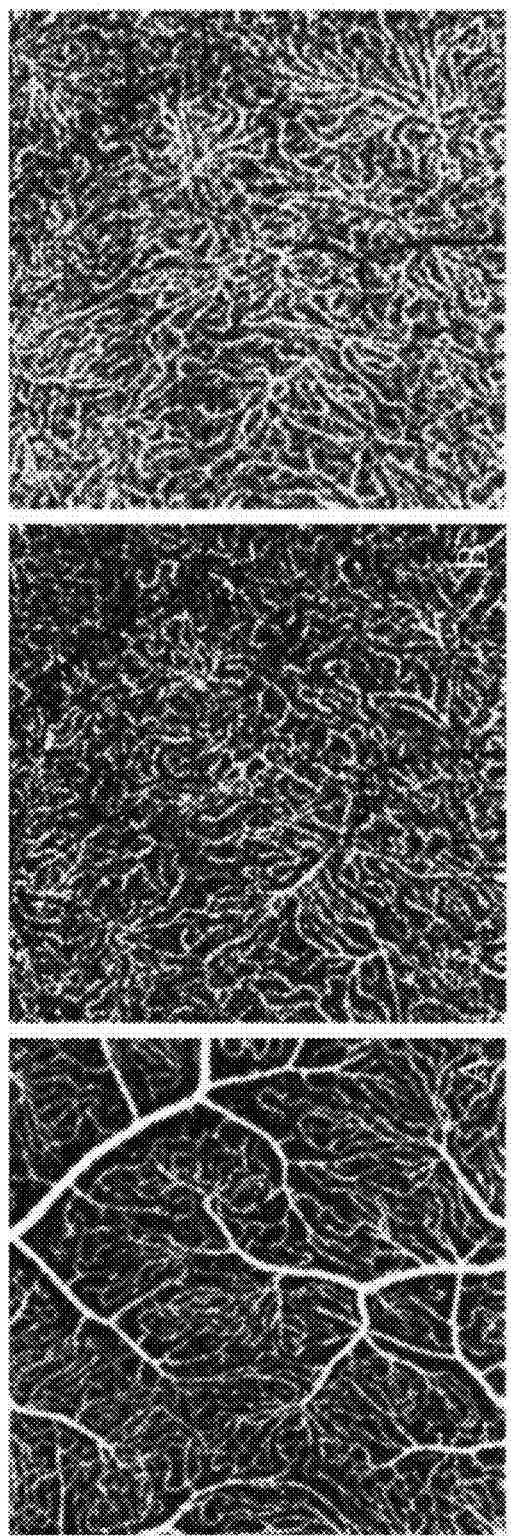
FIGS. 8A-8C illustrate en face maximum projection of rbPR-OCTA in superficial vascular plexus (FIG. 8A), intermediate capillary plexus (FIG. 8B), and deep capillary plexus (FIG. 8C), in accordance with various embodiments.

FIG. 8 shows the final results of rbPR-OCTA of the example described herein. FIG. 8 shows images of en face maximum projection of rbPR-OCTA in superficial vascular plexus (FIG. 8A), intermediate capillary plexus (FIG. 8B), and deep capillary plexus (FIG. 8C).

Using the acquisition method outlined above, 15 healthy participants, one participant with neovascular age-related macular degeneration and one participant with proliferative diabetic retinopathy were imaged. The diagnosis of the diseased eyes was based on clinical examination, and fluorescein angiography. The participants were enrolled after an informed consent in accordance with an Institutional Review Board approved protocol at Oregon Health and Science University. The study was conducted in compliance with the Declaration of Helsinki.

The images were processed using the PR-OCTA and by the rbPR-OCTA described herein. Angiograms were segmented into four slabs: superficial, intermediate, and deep retinal plexuses, and the outer retinal slab using structural OCT boundaries. The superficial layer was defined as inner 80% of ganglion cell complex (GCC) which includes all structures between the internal limiting membrane and inner plexiform layer (IPL)/inner nuclear layer (INL) border. The intermediate layer was defined as the outer 20% of GCC and the inner 50% of INL. The deep plexus was defined as the remaining slab internal to the outer boundaries of the outer plexiform layer (OPL). The outer retinal slab was defined as including outer nuclear layer (ONL), photoreceptor layer, the retinal pigment epithelium (RPE), and ending at the Bruch's membrane (BM).

In conventional clinical OCTA, the vascular pattern in the overlaying layers is duplicated in all deeper slabs (see FIG. 9C1). Using PR methods, it is possible to visualize 3 distinct vascular plexuses. Compared to prior PR methods, rbPR vascular patterns in intermediate plexuses (see FIG. 9B3) and deep plexuses (see FIG. 9C3) are better preserved while persistent projection artifacts are suppressed (see FIG. 9D3). To evaluate this quantitatively, the vascular skeleton area, vascular connectivity and flow single-to-noise ratio (fSNR) were assessed in 15 normal eyes from 15 study participants.

First, the superficial, intermediate and deep plexus angiograms obtained by two different PR methods were converted to binary images based on the thresholds determined from the mean plus 3 standard deviations of the values within their foveal avascular zone (FAZ). Then vascular skeletons (1-pixel wide lines) were detected using a thinning methodology algorithm (see, e.g., L. Lam, S-W Lee, and C. Y. Suen, "Thinning methodologies—a comprehensive survey," IEEE Transactions on pattern analysis and machine intelligence 14 (9), 869-885 (1992), incorporated by reference herein). Vascular skeleton area is defined as the total area of the skeleton network on en face angiograms. Vascular connectivity is defined as the ratio of the number of connected skeleton pixels to the total number of skeleton pixels. In this step, the connected pixels are detected if the number of the pixel group is larger than five. fSNR was calculated from the angiograms as $$fSNR = \frac{M_{parafovea} - M_{FAZ}}{\sigma_{FAZ}} \quad (6)$$

where, $M_{parafovea}$ and $M_{FAZ}$ are the mean values within parafoveal annulus shown in blue and FAZ shown in white (FIG. 9A1), respectively, and $\sigma_{FAZ}$ is the standard deviation of values within FAZ.

To quantitate the remaining artifact level, important in accurate detection and quantification of choroidal neovascularization in the normally avascular outer retinal slab, the remaining artifacts in outer retina were calculated as normalized by inner retinal flow signal in parafovea, as $$RA = \frac{M_{Outer} + 3 \times \sigma_{Outer}}{M_{Inner} + 3 \times \sigma_{Inner}} \quad (7)$$

where, $M_{outer}$ and $M_{inner}$ are the mean values of outer and inner retina within the parafovea, $\sigma_{Outer}$ and $\sigma_{Inner}$ are the standard deviation of values of the outer and inner retina within the parafovea.

The rbPR method showed improvement over prior PR-OCTA in vascular skeleton area, vascular connectivity and fSNR on three plexuses angiograms and the decrease in remaining artifacts on outer retinal angiogram from the 15 healthy subjects (see Table 1).

TABLE 1 comparison between prior PR and rbPR on quantitative metrics

| | | PR | rbPR | improvement |
|---|---|---|---|---|
| Superficial | VSA (mm²) | 1.79 ± 0.21 | 2.30 ± 0.24 | 64.55% |
| | VC | 0.96 ± 0.02 | 0.98 ± 0.01 | 2.08% |
| | fSNR | 3.82 ± 0.91 | 5.85 ± 1.60 | 53.14% |
| Intermediate | VSA (mm²) | 1.96 ± 0.24 | 2.54 ± 0.15 | 29.59% |
| | VC | 0.93 ± 0.03 | 0.98 ± 0.01 | 5.37% |
| | fSNR | 3.21 ± 0.92 | 5.82 ± 1.67 | 81.3% |
| Deep | VSA (mm²) | 1.29 ± 0.34 | 1.93 ± 0.65 | 49.61% |
| | VC | 0.80 ± 0.08 | 0.95 ± 0.05 | 18.75% |
| | fSNR | 1.49 ± 0.80 | 4.6 ± 1.74 | 208.72% |
| Outer | RA | 0.50 ± 0.09 | 0.37 ± 0.05 | 25.92% |

As shown in Table 1, VSA refers to Vascular Skeleton Area, VC refers to Vascular Connectivity, fSNR refers to flow signal-to-noise ratio, and RA refers to Remaining Artifact.

In various embodiments, rbPR-OCTA may be used for preservation of choroidal vascularization in age-related macular degeneration. With OCTA, choroidal vascularization (CNV) is detected as the presence of pathologic vessels in the normally avascular outer retinal slab. OCTA-derived quantitative metrics are important for assessing the effectiveness of anti-angiogenic therapy and monitoring recurrent growth of CNV. The vascular integrity is critical in accurately detecting CNV.

PR-OCTA removes strong projection artifacts in the RPE layer while preserving the CNV. However, the vascular continuity of the CNV was not always preserved and the background noise remained (see FIG. 10B1). The rbPR method (FIG. 10C1) suppresses the background noise better and delineates CNV with better vascular integrity than PR-OCTA. This result may be used with additional image processing steps, such as a saliency-based algorithm, to further remove the background noise and detect the CNV network.

The cross-sectional angiograms of CNV are critical in classifying the type of CNV anatomically. This is difficult to do without projection removal, as unprocessed OCTA (see FIG. 10A2) shows artefactual flow both above and below the RPE making classification difficult. The PR method facilitated the interpretation of CNV classification by removing these artifacts. The rbPR technique demonstrates sub-RPE flow more clearly, classifying the lesion as type 1 CNV. This is consistent with the FA diagnosis.

Furthermore, the rbPR-OCTA method may preserve retinal deeper plexuses in diabetic retinopathy. The ability to observe abnormalities in individual capillary networks may enable earlier detection of diabetic retinopathy. The deeper plexus slabs in conventional OCTA (see FIGS. 11B1 and 11C1) have significant projection artifacts, making interpretation difficult. PR-OCTA discriminates between three distinct retinal plexuses. In diabetic retinopathy, vascular abnormalities have been detected within each individual plexuses with PR-OCTA, findings not possible with conventional OCTA.

In a diabetic retinopathy case, applying prior PR-OCTA with lower resolution 6×6 mm scans reduces projecton artifact at the expense of reduced vessel connectivity in the deep capillary plexus (see FIGS. 11B2 and 11C2). In contrast, rbPR (FIGS. 11B3 and 11C3) results in maintained vessel integrity and improved contrast, features important for detecting and quantifying deep capillary plexus abnormalities.

Additionally, the rbPR-OCTA method may preserve the choriocapillaris. The choriocapillaris plays an important role in many macular diseases. However, in vivo imaging of the choriocapillaris using OCTA is hindered by projection artifacts. The PR method applied to the choriocapillaris slab (BM to 15 μm below) at central macula (see FIG. 12B1) suppressed these artifacts. The rbPR also suppresses these projection artifacts (see FIG. 12C1) but shows a denser and more continuous mesh-like vascular network with small black pores where blood flow is absent, which better reflects the known scanning electron microscopy description of the vasculature (e.g., as depicted in FIG. 12E).

Figure 13:
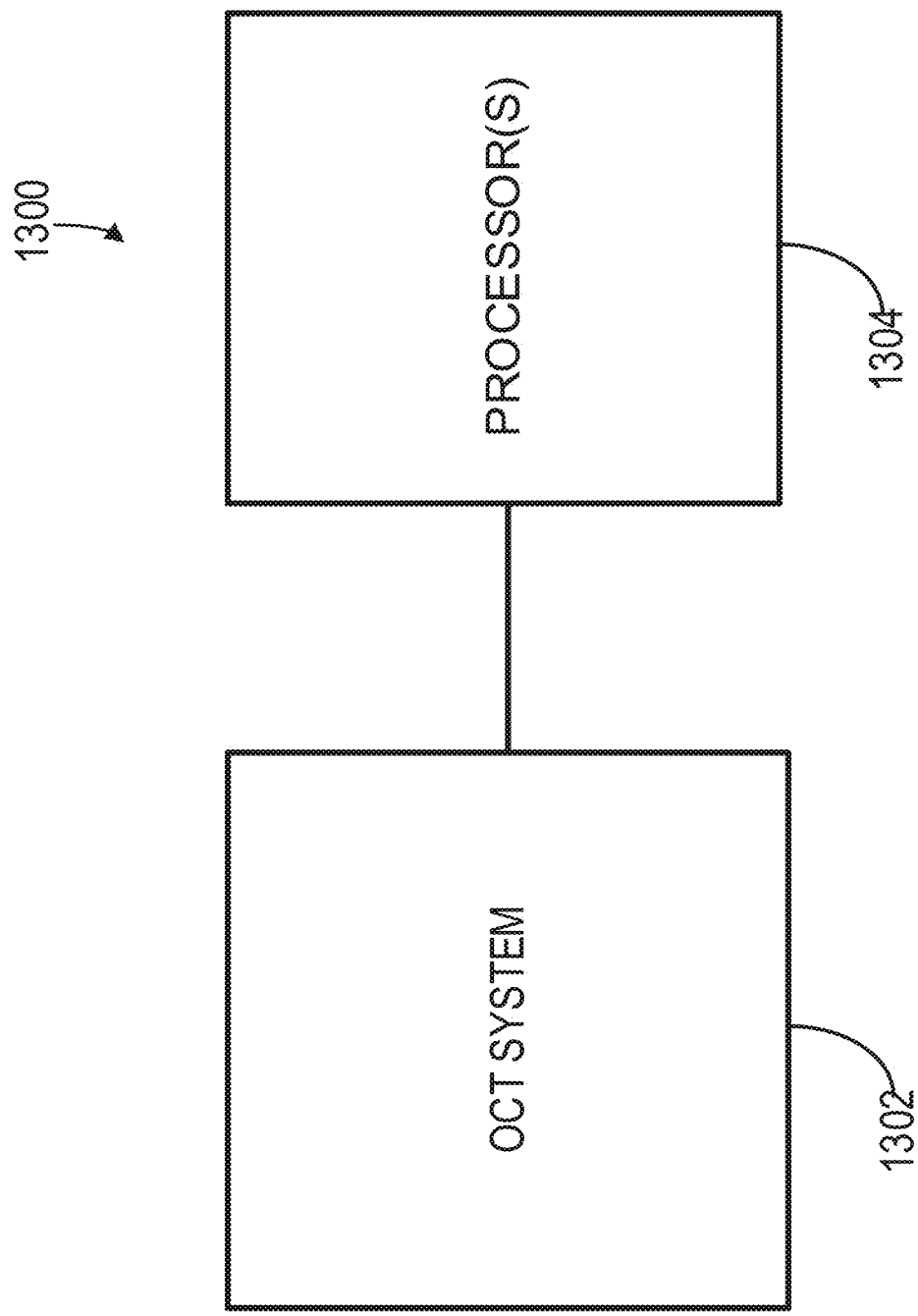
FIG. 13 schematically shows an example system processing OCT datasets to suppress shadowgraphic flow projections in OCT angiography datasets in accordance with the disclosure.

FIG. 13 schematically shows an example system 1300 for OCT angiography image processing in accordance with various embodiments. System 1300 comprises an OCT system 1302 configured to acquire an OCT image comprising OCT interferograms and one or more processors or computing systems 1304 that are configured to implement the various processing routines described herein. OCT system 1302 may comprise an OCT system suitable for OCT angiography applications, e.g., a swept source OCT system. For example, the OCT system 1302 may include all or selected aspects of the system 1500 shown in FIG. 15. In some embodiments, the processor(s) 1304 shown in FIG. 13 may correspond to the computer 1520 shown in FIG. 15.

In various embodiments, an OCT system may be adapted to allow an operator to perform various tasks. For example, an OCT system may be adapted to allow an operator to configure and/or launch various ones of the herein described methods. In some embodiments, an OCT system may be adapted to generate, or cause to be generated, reports of various information including, for example, reports of the results of scans run on a sample.

In embodiments of OCT systems comprising a display device, data and/or other information may be displayed for an operator. In embodiments, a display device may be adapted to receive an input (e.g., by a touch screen, actuation of an icon, manipulation of an input device such as a joystick or knob, etc.) and the input may, in some cases, be communicated (actively and/or passively) to one or more processors. In various embodiments, data and/or information may be displayed, and an operator may input information in response thereto.

In some embodiments, the above described methods and processes may be tied to a computing system, including one or more computers. In particular, the methods and processes described herein may be implemented as a computer application, computer service, computer API, computer library, and/or other computer program product.

Figure 14:
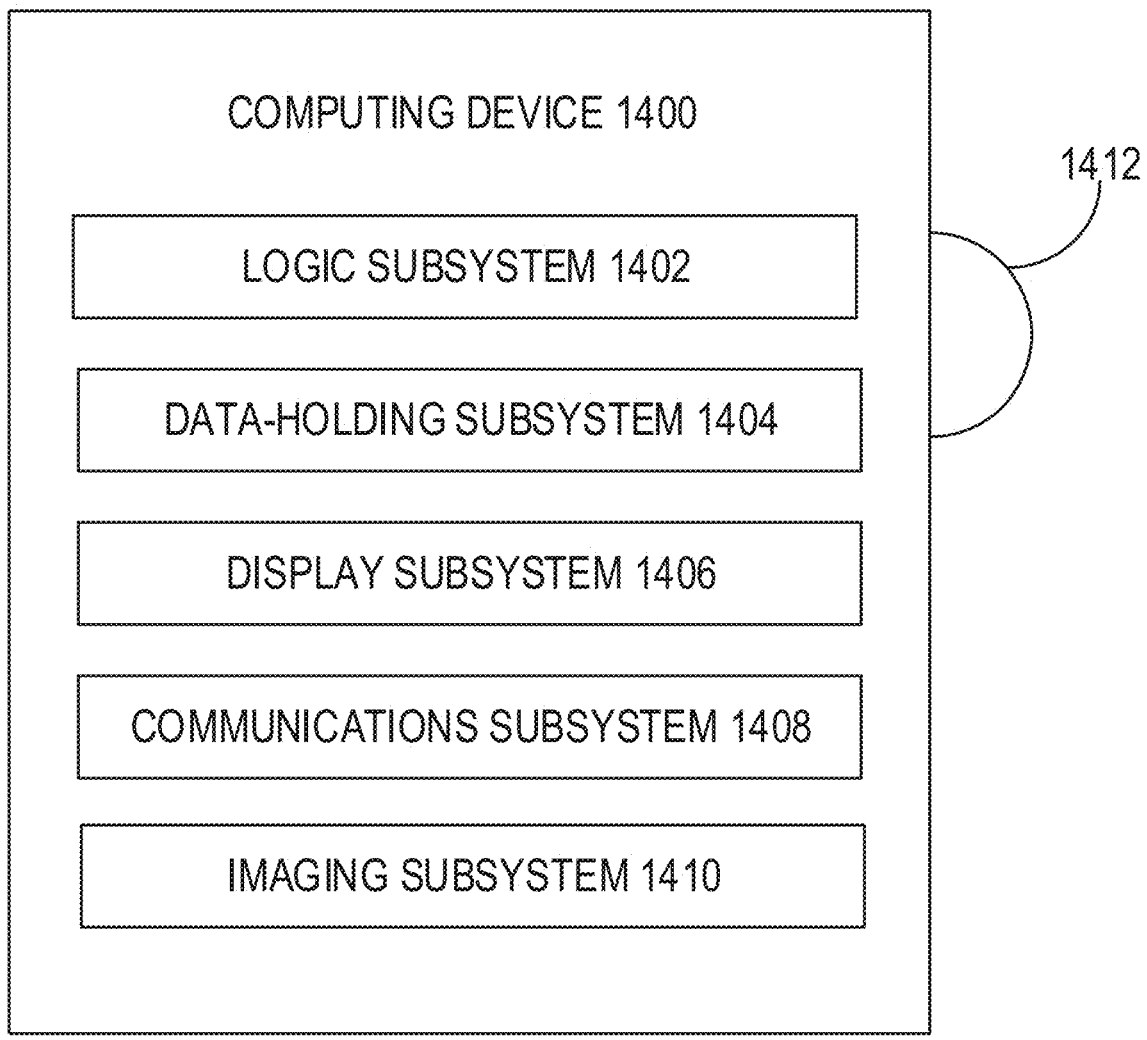
FIG. 14 schematically shows an example of a computing system in accordance with the disclosure.

FIG. 14 schematically shows a non-limiting computing device 1400 that may perform one or more of the above described methods and processes. For example, computing device 1400 may represent a processor 1304 included in system 1300 described above, and may be operatively coupled to, in communication with, or included in an OCT system (e.g., OCT image acquisition apparatus). Computing device 1400 is shown in simplified form. It is to be understood that virtually any computer architecture may be used without departing from the scope of this disclosure. In different embodiments, computing device 1400 may take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1400 includes a logic subsystem 1402 and a data-holding subsystem 1404. Computing device 1400 may optionally include a display subsystem 1406, a communication subsystem 1408, an imaging subsystem 1410, and/or other components not shown in FIG. 14. Computing device 1400 may also optionally include user input devices such as manually actuated buttons, switches, keyboards, mice, game controllers, cameras, microphones, and/or touch screens, for example.

Logic subsystem 1402 may include one or more physical devices configured to execute one or more machine-readable instructions. For example, the logic subsystem may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem may include one or more processors that are configured to execute software instructions. For example, the one or more processors may comprise physical circuitry programmed to perform various acts described herein. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Data-holding subsystem 1404 may include one or more physical, non-transitory, devices configured to hold data and/or instructions executable by the logic subsystem to implement the herein described methods and processes. When such methods and processes are implemented, the state of data-holding subsystem 1404 may be transformed (e.g., to hold different data).

Data-holding subsystem 1404 may include removable media and/or built-in devices. Data-holding subsystem 1404 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1404 may include devices with one or more of the following characteristics: volatile, nonvolatile, dynamic, static, read/write, read-only, random access, sequential access, location addressable, file addressable, and content addressable. In some embodiments, logic subsystem 1402 and data-holding subsystem 1404 may be integrated into one or more common devices, such as an application specific integrated circuit or a system on a chip.

FIG. 14 also shows an aspect of the data-holding subsystem in the form of removable computer-readable storage media 1412, which may be used to store and/or transfer data and/or instructions executable to implement the herein described methods and processes. Removable computer-readable storage media 1412 may take the form of CDs, DVDs, HD-DVDs, Blu-Ray Discs, EEPROMs, flash memory cards, USB storage devices, and/or floppy disks, among others.

When included, display subsystem 1406 may be used to present a visual representation of data held by data-holding subsystem 1404. As the herein described methods and processes change the data held by the data-holding subsystem, and thus transform the state of the data-holding subsystem, the state of display subsystem 1406 may likewise be transformed to visually represent changes in the underlying data. Display subsystem 1406 may include one or more display devices utilizing virtually any type of technology. Such display devices may be combined with logic subsystem 1402 and/or data-holding subsystem 1404 in a shared enclosure, or such display devices may be peripheral display devices.

When included, communication subsystem 1408 may be configured to communicatively couple computing device 1400 with one or more other computing devices. Communication subsystem 1408 may include wired and/or wireless communication devices compatible with one or more different communication protocols. As non-limiting examples, the communication subsystem may be configured for communication via a wireless telephone network, a wireless local area network, a wired local area network, a wireless wide area network, a wired wide area network, etc. In some embodiments, the communication subsystem may allow computing device 1400 to send and/or receive messages to and/or from other devices via a network such as the Internet.

When included, imaging subsystem 1410 may be used acquire and/or process any suitable image data from various sensors or imaging devices in communication with computing device 1400. For example, imaging subsystem 1410 may be configured to acquire OCT image data, e.g., interferograms, as part of an OCT system, e.g., OCT system 1302 described above. Imaging subsystem 1410 may be combined with logic subsystem 1402 and/or data-holding subsystem 1404 in a shared enclosure, or such imaging subsystems may comprise periphery imaging devices. Data received from the imaging subsystem may be held by data-holding subsystem 1404 and/or removable computer-readable storage media 1412, for example.

Figure 15:
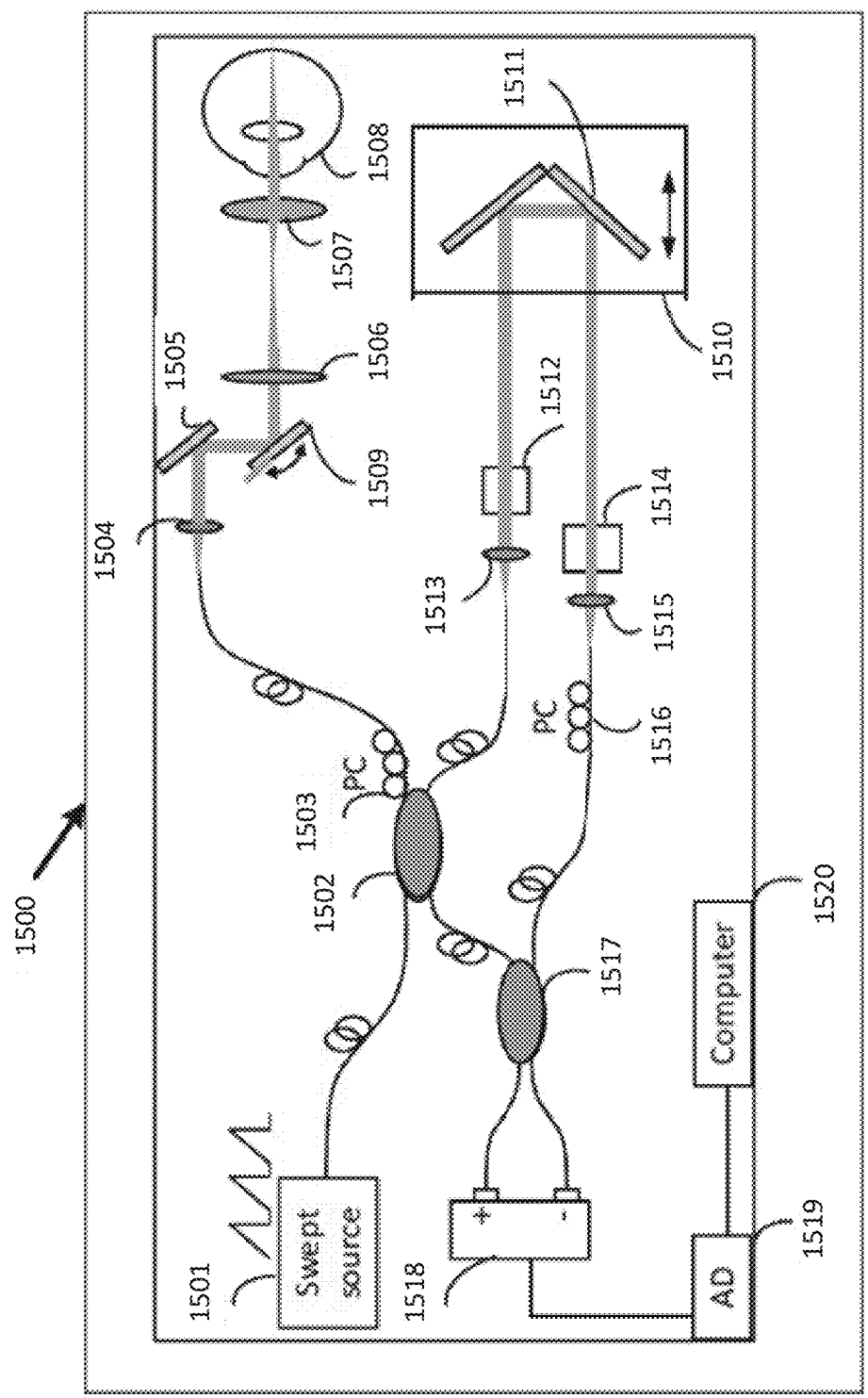
FIG. 15 schematically shows an OCT system that may be used to practice various embodiments disclosed herein.

FIG. 15 schematically illustrates an in vivo imaging system 1500 for collecting OCT image information. In some embodiments, the system 1500 may correspond to the system 1300 shown in FIG. 13. For example, the computer 1520 may correspond to the one or more processors 1304, and some or all of the remaining components of system 1500 may correspond to the OCT system 1302 of FIG. 13.

The system 1500 may be, for example, a high-speed swept-source OCT system 1500 (e.g., as described in B. Potsaid, B. Baumann, D. Huang, S. Barry, A. E. Cable, J. S. Schuman, J. S. Duker, and J. G. Fujimoto, "Ultrahigh speed 1050 nm swept source/fourier domain oct retinal and anterior segment imaging at 100,000 to 400,000 axial scans per second," Opt. Express 18(19), 20029-20048 (2010)) can used to demonstrate the methods described herein. High speed swept-source OCT system 1500 comprises a tunable laser 1501. For example, tunable laser 1501 (e.g., a tunable laser from Axsun Technologies, Inc., Billerica, Mass., USA) may have a wavelength of 1050 nm with 100 nm tuning range, a tuning cycle with a repetition rate of 100 kHz and a duty cycle of 50%. Such OCT system 1500 can produce a measured axial resolution of 5.3 µm (full-width-half-maximum amplitude profile) and an imaging range of 2.9 mm in tissue. Light from swept source 1501 can be coupled into a two by two fiber coupler 1502 through single mode optical fiber. One portion of the light (e.g., 70%) can proceed to the sample arm (i.e., the patient interface), and the other portion of the light (e.g., 30%) can proceed to the reference arm.

In the sample arm, a sample arm polarization control unit 1503 can be used to adjust light polarization state. The exit light from the fiber coupler 1502 can then be coupled with a retinal scanner whereby the light is collimated by sample arm collimating lens 1504 and reflected by mirror 1505 and two dimensional galvo scanner 1509 (e.g., an XY galvo-nanometer scanner). Two lenses, first lens 1506 (e.g., an objective lens) and second lens 1507 (e.g., an ocular lens) can relay probe beam reflected by galvo scanner 1509 into a human eye 1508. For example, a focused spot diameter of 18 µm (full-width-half-maximum amplitude profile) can be calculated on the retinal plane based on an eye model. The average light power (i.e., output power of the laser) onto a human eye can be 1.9 mW, which is consistent with safe ocular exposure limit set by the American National Standard Institute (ANSI).

The reference arm can comprise a first reference arm collimating lens 1513, a water cell 1512, a retro-reflector 1511, a glass plate 1514 and a second reference arm collimating lens 1515. Glass plate 1514 can be used to balance the dispersion between the OCT sample arm and reference arm. Water cell 1512 can be used to compensate the influence of dispersion in the human eye 1508. Retro-reflector 1511 can be mounted on a translation stage 1510 which can be moved to adjust the path length in the reference arm.

Light from the sample and reference arm can interfere at beam splitter 1517. A reference arm polarization control unit 1516 can be used to adjust the beam polarization state in the reference arm to maximum interference signal. The optical interference signal from beam splitter 1517 (e.g., a 50/50 coupler) can be detected by a balanced detector 1518 (e.g., a balanced receiver manufactured by Thorlabs, Inc., Newton, N.J., USA), sampled by an analog digital conversion unit 1519 (e.g., a high speed digitizer manufactured by Innovative Integration, Inc.) and transferred into computer 1520 for processing. For example, computer 1520 can be used for storing instructions for, and implementing, the methods described herein. Interference fringes, for example, can be recorded by analog digital conversion unit 1519 at 400 MHz with 14-bit resolution, with the acquisition driven by the optical clock output of tunable laser 1501. In such an exemplary setup, imaging system 1500, sensitivity can be measured with a mirror and neutral density filter at 95 dB, with a sensitivity roll-off of 4.2 dB/mm.

While a swept-source OCT system has been described above, the technology disclosed herein can be applied to any Fourier-domain OCT system. In Fourier-domain OCT systems the reference mirror is kept stationary and the interference between the sample and reference reflections are captured as spectral interferograms, which are processed by Fourier-transform to obtain cross-sectional images. In the spectral OCT implementation of Fourier-domain OCT, a broad band light source is used and the spectral interferogram is captured by a grating or prism-based spectrometer. The spectrometer uses a line camera to detect the spectral interferogram in a simultaneous manner. In the swept-source OCT implementation of Fourier-domain OCT, the light source is a laser that is very rapidly and repetitively tuned across a wide spectrum and the spectral interferogram is captured sequentially. Swept-source OCT can achieve higher speed and the beam can be scanned transversely more rapidly (with less spot overlap between axial scans) without suffering as much signal loss due to fringe washout compared to other Fourier-domain OCT systems. However, a very high speed spectral OCT system could also be utilized with the technology disclosed herein.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method for suppressing shadowgraphic flow projection artifacts in an optical coherence tomography (OCT) angiography dataset, comprising:
    obtaining a structural OCT dataset;
    separating the structural OCT dataset into multiple clusters according to respective reflectance values;
    generating contrast enhanced C-scans for individual clusters of the multiple clusters to obtain a contrast enhanced dataset according to:

$$I_e(i) = \begin{cases} B_1 \times \sum_{n=0}^{I(i)} \frac{H_c(n)}{N_L}, & 0 \le I(i) \le B_1 \\ (B_1+1) + (B_2 - B_1 + 1) \sum_{n=B_1+1}^{I(i)} \frac{H_c(n)}{N_M}, & B_1+1 \le I(i) \le B_2 \\ (B_2+1) + (L - B_2 + 1) \sum_{n=B_2+1}^{I(i)} \frac{H_c(n)}{N_H}, & B_2+1 \le I(i) \end{cases}$$

where $I_e$ is the contrast enhanced C-scan, $B_1$ and $B_2$ are reflectance values of boundary points between the multiple clusters, $H_c(n)$ is a corresponding C-scan of the structural OCT dataset, $N_L$, $N_M$ and $N_H$ are numbers of pixels belonging to respective clusters of the multiple clusters, n is a gray value of reflectance, and L is a gray level;
    suppressing projection artifacts in an OCT angiography (OCTA) dataset based on the contrast enhanced dataset to obtain a projection resolved OCTA dataset; and
    generating an image based on the projection resolved OCTA dataset.

2. The method of claim 1, wherein the structural OCT dataset is separated into the multiple clusters by K-means classification.

3. The method of claim 1, further comprising separating the structural OCT dataset into a first sub-volume and a second sub-volume based on a photoreceptor inner/outer segment boundary, wherein the separating the structural OCT dataset into multiple clusters, the generating the contrast enhanced C-scans, and the suppressing projection artifacts are performed separately for the first and second sub-volumes.

4. The method of claim 1, wherein the suppressing projection artifacts in the OCTA dataset based on the contrast enhanced dataset to obtain a projection resolved OCTA dataset is performed according to:

$$A_1 = A_0 \times \text{normalized}(V_e),$$

where $A_1$ is the projection resolved OCTA dataset, $A_0$ is the OCTA dataset, and $V_e$ is the contrast enhanced dataset.

5. The method of claim 1, further comprising:
    generating a vessel probability map; and
    generating a vessel enhanced OCTA dataset based on the projection resolved OCTA dataset and the vessel probability map.

6. The method of claim 5, wherein the generating the vessel probability map includes assigning a probability for individual pixels of the structural OCT dataset with a reflectance value between a boundary value ($B_1$) that defines a high reflectance cluster of the multiple clusters, and a center value ($C_H$) of the high reflectance cluster, wherein the assigned probability corresponds to a probability of the respective pixel belonging to the high reflectance cluster.

7. The method of claim 6, wherein the generating the vessel probability map further includes assigning pixels of the structural OCT dataset having reflectance values outside the range of $B_1$ to $C_H$ a probability of 0.

8. The method of claim 1, wherein the multiple clusters comprise three clusters corresponding to a relative high reflectance, medium reflectance, and low reflectance, respectively.

9. A system for generating reflectance-based projection-resolved (rbPR) optical coherence tomography (OCT) angiography data, comprising:
an OCT system configured to acquire a structural OCT dataset of a sample;
a logic subsystem; and
a data holding subsystem comprising machine-readable instructions stored thereon that are executable by the logic subsystem to:
separate the structural OCT dataset into multiple clusters according to respective reflectance values;
generate contrast enhanced C-scans for individual clusters of the multiple clusters to obtain a contrast enhanced dataset according to:

$$I_e(i) = \begin{cases} B_1 \times \sum_{n=0}^{I(i)} \frac{H_c(n)}{N_L}, & 0 \le I(i) \le B_1 \\ (B_1+1)+(B_2-B_1+1)\sum_{n=B_1+1}^{I(i)} \frac{H_c(n)}{N_M}, & B_1+1 \le I(i) \le B_2 \\ (B_2+1)+(L-B_2+1)\sum_{n=B_2+1}^{I(i)} \frac{H_c(n)}{N_H}, & B_2+1 \le I(i) \end{cases}$$

where $I_e$ is the contrast enhanced C-scan, $B_1$ and $B_2$ are reflectance values of boundary points between the multiple clusters, $H_c(n)$ is a corresponding C-scan of the structural OCT dataset, $N_L$, $N_M$ and $N_H$ are numbers of pixels belonging to respective clusters of the multiple clusters, n is a gray value of reflectance, and L is a gray level;
suppress projection artifacts in an OCT angiography (OCTA) dataset based on the contrast enhanced dataset to obtain a projection resolved OCTA dataset; and
generate an image based on the projection resolved OCTA dataset.

10. The system of claim 9, wherein the structural OCT dataset is separated into the multiple clusters by K-means classification.

11. The system of claim 9, wherein the instructions are further executable by the logic subsystem to separate the structural OCT dataset into a first sub-volume and a second sub-volume based on a photoreceptor inner/outer segment boundary, and wherein the logic subsystem is to separate of the structural OCT dataset into multiple clusters, generate the contrast enhanced C-scans, and suppress the projection artifacts separately for the first and second sub-volumes.

12. The system of claim 9, wherein the logic subsystem is to suppress the projection artifacts in the OCTA dataset based on the contrast enhanced dataset to obtain a projection resolved OCTA dataset according to:

$$A_1 = A_0 \times \text{normalized}(V_e),$$

where $A_1$ is the projection resolved OCTA dataset, $A_0$ is the OCTA dataset, and $V_e$ is the contrast enhanced dataset.

13. The system of claim 9, wherein the instructions are further executable by the logic subsystem to:
generate a vessel probability map; and
generate a vessel enhanced OCTA dataset based on the projection resolved OCTA dataset and the vessel probability map.

14. The system of claim 13, wherein, to generate the vessel probability map, the instructions are executable by the logic subsystem to assign a probability for individual pixels of the structural OCT dataset with a reflectance value between a boundary value ($B_1$) that defines a high reflectance cluster of the multiple clusters, and a center value ($C_H$) of the high reflectance cluster, wherein the assigned probability corresponds to a probability of the respective pixel belonging to the high reflectance cluster.

15. The system of claim 14, wherein, to generate the vessel probability map, the instructions are further executable by the logic subsystem to assign pixels of the structural OCT dataset having reflectance values outside the range of $B_1$ to $C_H$ a probability of 0.

16. The system of claim 9, wherein the multiple clusters comprise three clusters corresponding to a relative high reflectance, medium reflectance, and low reflectance, respectively.

* * * * *